US009835965B2

(12) United States Patent
Okubo et al.

(10) Patent No.: US 9,835,965 B2
(45) Date of Patent: Dec. 5, 2017

(54) CHARGE CONTROL AGENT AND TONER USING SAME

(71) Applicant: HODOGAYA CHEMICAL CO., LTD., Tokyo (JP)

(72) Inventors: Masaki Okubo, Ibaraki (JP); Ikuo Kimura, Ibaraki (JP); Masami Ito, Tokyo (JP); Motonori Tsuji, Tokyo (JP); Takeshi Yamamoto, Tokyo (JP); Masaya Tojo, Ibaraki (JP); Masafumi Asakai, Tokyo (JP); Tetsuya Yoshida, Tokyo (JP)

(73) Assignee: HODOGAYA CHEMICAL CO., LTD., Tokyo (JP)

( * ) Notice: Subject to any disclaimer, the term of this patent is extended or adjusted under 35 U.S.C. 154(b) by 0 days.

(21) Appl. No.: 15/024,743

(22) PCT Filed: Sep. 24, 2014

(86) PCT No.: PCT/JP2014/075216
§ 371 (c)(1),
(2) Date: Mar. 24, 2016

(87) PCT Pub. No.: WO2015/046214
PCT Pub. Date: Apr. 2, 2015

(65) Prior Publication Data
US 2016/0216628 A1 Jul. 28, 2016

(30) Foreign Application Priority Data

Sep. 24, 2013 (JP) ................................ 2013-196378

(51) Int. Cl.
*G03G 9/08* (2006.01)
*G03G 9/097* (2006.01)
*C07D 401/14* (2006.01)
*C07D 417/14* (2006.01)
*C07D 209/48* (2006.01)
*C07D 403/10* (2006.01)
*C07D 403/12* (2006.01)
*G03G 9/087* (2006.01)
*G03G 9/09* (2006.01)

(52) U.S. Cl.
CPC ....... *G03G 9/09758* (2013.01); *C07D 209/48* (2013.01); *C07D 401/14* (2013.01); *C07D 403/10* (2013.01); *C07D 403/12* (2013.01); *C07D 417/14* (2013.01); *G03G 9/081* (2013.01); *G03G 9/0819* (2013.01); *G03G 9/08711* (2013.01); *G03G 9/0904* (2013.01)

(58) Field of Classification Search
CPC . G03G 9/09758; C07D 209/48; C07D 417/14
USPC .................................................. 430/108.21
See application file for complete search history.

(56) References Cited

U.S. PATENT DOCUMENTS

| 254,028 A | 2/1882 | Lasher |
| 327,140 A | 9/1885 | Harris |
| 327,294 A | 9/1885 | McFadden et al. |
| 4,206,064 A | 6/1980 | Kiuchi et al. |
| 4,338,390 A | 7/1982 | Lu |
| 4,403,027 A | 9/1983 | Ishikawa et al. |
| 4,767,688 A | 8/1988 | Hashimoto et al. |
| 5,049,467 A | 9/1991 | Yamanaka |
| 5,225,305 A | 7/1993 | Kiyoyanagi et al. |
| 5,413,888 A | 5/1995 | Sacripante et al. |

FOREIGN PATENT DOCUMENTS

| EP | 0227874 A1 | 7/1987 |
| EP | 0242420 A1 | 10/1987 |
| EP | 0712049 A1 | 5/1996 |
| JP | S5542752 B2 | 11/1980 |
| JP | S57111541 A | 7/1982 |
| JP | S57119364 A | 7/1982 |
| JP | S589154 A | 1/1983 |
| JP | S5898742 A | 6/1983 |
| JP | S61003149 A | 1/1986 |
| JP | S6169073 A | 4/1986 |
| JP | S61141453 A | 6/1986 |
| JP | S61221756 A | 10/1986 |
| JP | S6294856 A | 5/1987 |
| JP | H01306861 A | 12/1989 |
| JP | H04107569 A | 4/1992 |
| JP | H05297614 A | 11/1993 |
| JP | H05307272 A | 11/1993 |
| JP | H05307273 A | 11/1993 |
| JP | H07056393 A | 3/1995 |
| JP | H07175231 A | 7/1995 |
| JP | H07179423 A | 7/1995 |
| JP | 2568675 B2 | 1/1997 |
| JP | 2899038 B2 | 3/1999 |
| JP | 2001154413 A | 6/2001 |
| JP | 3313871 B2 | 8/2002 |
| JP | 3325730 B2 | 9/2002 |
| JP | 3359657 B2 | 12/2002 |
| JP | 2003162100 A | 6/2003 |
| JP | 2003295522 A | 10/2003 |

(Continued)

OTHER PUBLICATIONS

International Search Report in International Application No. PCT/JP2014/075216, filed Sep. 24, 2014.

*Primary Examiner* — Mark A Chapman
(74) *Attorney, Agent, or Firm* — Saliwanchik, Lloyd & Eisenschenk

(57) ABSTRACT

To provide a charge control agent and a toner having a superior charging characteristic. A charge control agent containing a bis-phthalimide derivative represented by formula. Thus, it is possible to provide a safe, negative chargeability charge control agent with which the rate of rise of the charge can be increased, and which has a high charging amount and poses no problem in terms of waste regulations. Furthermore, it is possible to provide a negatively chargeable toner (and particularly, a negatively chargeable polymerized toner) for electrostatic image development which uses this charging control agent and has a superior charging characteristic.

9 Claims, No Drawings

(56) References Cited

FOREIGN PATENT DOCUMENTS

| WO | WO-2007111346 A1 | 10/2007 |
| WO | WO-2007119797 A1 | 10/2007 |

CHARGE CONTROL AGENT AND TONER USING SAME

CROSS-REFERENCE TO RELATED APPLICATION

This application is the U.S. national stage application of International Patent Application No. PCT/JP2014/075216, filed Sep. 24, 2014, which claims priority to Japanese Application No. 2013-196378, filed Sep. 24, 2013, the disclosures of each of which are incorporated herein by reference in their entirety.

TECHNICAL FIELD

The present invention relates to a charge control agent used in an image formation apparatus for image-developing an electrostatic latent image in an electrophotography or electrostatic recording field, and a negative chargeable toner containing the charge control agent.

BACKGROUND ART

In an image formation process by an electrophotographic system, an electrostatic latent image is formed on an inorganic photoreceptor such as selenium, a selenium alloy, cadmium sulfide and amorphous silicon or an organic photoreceptor using a charge generating agent and a charge transfer agent. The electrostatic latent image is developed with a toner, transferred to paper or a plastic film, and fixed to provide a visible image. The photoreceptor has a positive chargeability or a negative chargeability depending on its configuration. If a printed matter is left as the electrostatic latent image by exposure, it is developed with an opposite sign chargeable toner. On the other hand, if the printed matter is charge-removed and inverted, it is developed with a same sign chargeable toner.

The toner is configured of a binder resin, a coloring agent and other additives. In general, a charge control agent is added in order to add desirable charging properties (including a charging speed, a charging level and a charging stability), a temporal stability, and an environmental stability. By adding the charge control agent, the properties of the toner are greatly improved.

Examples of a positive friction chargeable charge control agent used in the technical field of interest include Nigrosine dye, azine based dye, a copper phthalocyanine pigment, a quaternary ammonium salt and a polymer having a quaternary ammonium salt in a side chain. On the other hand, as a negative friction chargeable charge control agent, a metal complex salt of monoazo dye, salicylic acid, naphthoic acid, a metal complex of dicarboxylic acid, a copper phthalocyanine pigment, and a resin including an acid component are used.

In a color toner of which market is expected to expand in the future, a light color that does not affect a hue, desirably a colorless, charge control agent is essential. Examples of the light color or colorless charge control agent for the negative chargeable toner include a metal complex salt compound of a hydroxybenzoic acid derivative (see Patent Documents 1 to 3, for example), a metal salt compound of aromatic dicarboxylic acid (see Patent Document 4, for example), a metal complex salt compound of an anthranilic acid derivative (see Patent Documents 5 to 6, for example), an organic boron compound (see Patent Documents 7 to 8, for example), a biphenol compound (see Patent Document 9, for example), a calix (n) arene compound (see Patent Documents 10 to 15, for example) and a cyclic phenol sulfide (see Patent Documents 16 to 18, for example). Examples of the positive chargeable toner include a quaternary ammonium salt compound (see Patent Documents 19 to 21, for example).

Patent Document 1: Japanese Patent Application Laid-open No. 55-042752
Patent Document 2: Japanese Patent Application Laid-open No. 61-069073
Patent Document 3: Japanese Patent Application Laid-open No. 61-221756
Patent Document 4: Japanese Patent Application Laid-open No. 57-111541
Patent Document 5: Japanese Patent Application Laid-open No. 61-141453
Patent Document 6: Japanese Patent Application Laid-open No. 62-094856
Patent Document 7: U.S. Pat. No. 4,767,688
Patent Document 8: Japanese Patent Application Laid-open No. 1-306861
Patent Document 9: Japanese Patent Application Laid-open No. 61-003149
Patent Document 10: Japanese Patent No. 2568675
Patent Document 11: Japanese Patent No. 2899038
Patent Document 12: Japanese Patent No. 3359657
Patent Document 13: Japanese Patent No. 3313871
Patent Document 14: Japanese Patent No. 3325730
Patent Document 15: Japanese Patent Application Laid-open No. 2003-162100
Patent Document 16: Japanese Patent Application Laid-open No. 2003-295522
Patent Document 17: PCT International Publication No. 2007-111346
Patent Document 18: PCT International Publication No. 2007-119797
Patent Document 19: Japanese Patent Application Laid-open No. 57-119364
Patent Document 20: Japanese Patent Application Laid-open No. 58-009154
Patent Document 21: Japanese Patent Application Laid-open No. 58-098742

SUMMARY OF INVENTION

Problem to be Solved by the Invention

However, many of these charge control agents are complexes or salts including heavy metals such as chromium that have a problem concerning the waste regulation, and are not necessarily safety. In addition, a charge imparting effect is low, and a charge rise speed is insufficient. Therefore, an initial copy image lacks sharpness, and quality of a copy image during successive copying easily changes. Furthermore, it has a disadvantage of being inapplicable to a polymerized toner. Accordingly, there is desirable to provide a charge control agent having a high charge imparting effect and being applicable to a polymerized toner.

In view of the above, an object of the present invention is to provide a negative chargeable charge control agent having a high charge rise speed and a high charge amount but having no problem concerning the waste regulation. Another object is to provide a negative chargeable toner for developing an electrostatic image, in particular, a negative chargeable polymerized toner, using the charge control agent having high charging properties.

Means for Solving the Problem

In order to achieve the above-described objects, a charge control agent according to an embodiment of the present invention includes a bisphthalimide derivative represented by a formula (1).

[Chemical Formula 1]

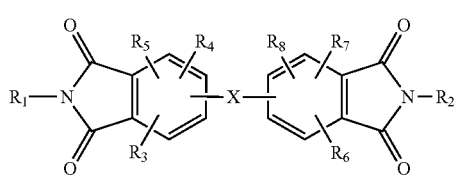

(1)

(where X represents a carbonyl group, a sulfur atom, a sulfinyl group, a sulfonyl group or a single bond; $R_1$ and $R_2$ each represents a linear or branched alkyl group having 1 to 20 carbon atoms, a cycloalkyl group having 5 to 10 carbon atoms, an aromatic hydrocarbon group, a heterocyclic group or a fused polycyclic aromatic group; $R_3$ to $R_8$ each represents a hydrogen atom, a deuterium atom, a halogen atom, a hydroxyl group, a cyano group, a trifluoromethyl group, a nitro group, a linear or branched alkyl group having 1 to 20 carbon atoms, a cycloalkyl group having 5 to 10 carbon atoms, a linear or branched alkenyl group having 2 to 6 carbon atoms, a linear or branched alkyloxy group having 1 to 8 carbon atoms, a cycloalkyloxy group having 5 to 10 carbon atoms, an aromatic hydrocarbon group, a heterocyclic group, a fused polycyclic aromatic group or an aryloxy group. Note that $R_1$ to $R_8$ each may have a substituent, and $R_3$ to $R_5$ and $R_6$ to $R_8$ may bond each other to form a ring.)

By the configuration that the bisphthalimide derivative represented by the formula (1) is included, there is provided a charge control agent having especially excellent charging properties including a high charge rise speed, a high charge amount and an environmental stability as compared with the charge control agent in the related art. In addition, the charge control agent contains no heavy metals that have a problem concerning the waste regulation, therefore can decrease a burden applied to human and environment, and has excellent dispersibility and a compound stability.

A charge control agent according to an embodiment of the present invention includes a bisphthalimide derivative represented by a formula (2).

[Chemical Formula 2]

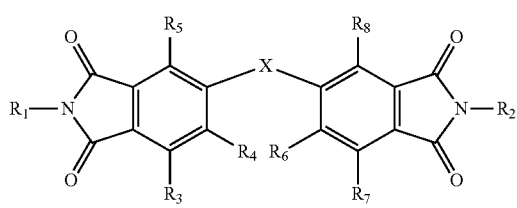

(2)

(where X represents a carbonyl group, a sulfur atom, a sulfinyl group, a sulfonyl group or a single bond; $R_1$ and $R_2$ each represents a linear or branched alkyl group having 1 to 20 carbon atoms, a cycloalkyl group having 5 to 10 carbon atoms, an aromatic hydrocarbon group, a heterocyclic group or a fused polycyclic aromatic group; $R_3$ to $R_8$ each represents a hydrogen atom, a deuterium atom, a halogen atom, a hydroxyl group, a cyano group, a trifluoromethyl group, a nitro group, a linear or branched alkyl group having 1 to 20 carbon atoms, a cycloalkyl group having 5 to 10 carbon atoms, an aromatic hydrocarbon group, a linear or branched alkenyl group having 2 to 6 carbon atoms, a linear or branched alkyloxy group having 1 to 8 carbon atoms, a cycloalkyloxy group having 5 to 10 carbon atoms, an aromatic hydrocarbon group, a heterocyclic group, a fused polycyclic aromatic group or an aryloxy group. Note that $R_1$ to $R_8$ each may have a substituent, and $R_3$ and $R_4$ may bond each other to form a ring and $R_6$ and $R_7$ may bond each other to form a ring.)

By the configuration that the bisphthalimide derivative represented by the formula (2) is included, there is provided a charge control agent having especially excellent charging properties including a high charge rise speed, a high charge amount and an environmental stability as compared with the charge control agent in the related art. In addition, the charge control agent contains no heavy metals that have a problem concerning the waste regulation, therefore can decrease a burden applied to human and environment, and has excellent dispersibility and a compound stability.

A charge control agent according to an embodiment of the present invention includes a bisphthalimide derivative represented by a formula (2').

[Chemical Formula 3]

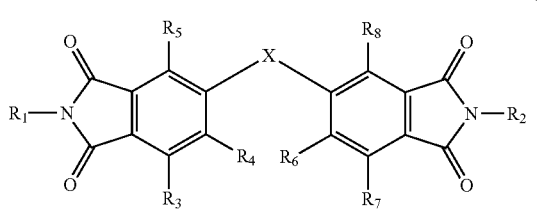

(2')

(where X represents a carbonyl group, a sulfonyl group or a single bond; $R_1$ and $R_2$ each represents a linear or branched alkyl group having 1 to 20 carbon atoms, a cycloalkyl group having 5 to 10 carbon atoms, an aromatic hydrocarbon group or a heterocyclic group; $R_3$ to $R_8$ each represents a hydrogen atom, a deuterium atom, a halogen atom, a hydroxyl group, a cyano group, a trifluoromethyl group, a nitro group, a linear or branched alkyl group having 1 to 20 carbon atoms, a cycloalkyl group having 5 to 10 carbon atoms, an aromatic hydrocarbon group, a linear or branched alkenyl group having 2 to 6 carbon atoms, a linear or branched alkyloxy group having 1 to 8 carbon atoms or an aromatic hydrocarbon group. Note that $R_1$ to $R_8$ each may have a substituent, and $R_3$ and $R_4$ may bond each other to form a ring and $R_6$ and $R_7$ may bond each other to form a ring.

By the configuration that the bisphthalimide derivative represented by the formula (2') is included, there is provided a charge control agent having especially excellent charging properties including a high charge rise speed, a high charge amount and an environmental stability as compared with the charge control agent in the related art. In addition, the charge control agent contains no heavy metals that have a problem concerning the waste regulation, therefore can decrease a burden applied to human and environment, and has excellent dispersibility and a compound stability.

A toner according to an embodiment of the present invention includes any of the above-described charge control agents, a coloring agent and a binder resin. By the configuration that the above-described charge control agent is included, there can be provided the toner having excellent charging properties and a low burden applied to human and environment.

A polymerized toner according to an embodiment of the present invention includes any of the above-described charge control agents, a coloring agent and a binder resin. By the configuration that the above-described charge control agent is included, there can be provided the polymerized toner having excellent charging properties and a low burden applied to human and environment.

Effect of the Invention

There can be provided a charge control agent and a toner having excellent charging properties and a low burden applied to human and environment.

MODES FOR CARRYING OUT THE INVENTION

[Toner]

A toner according to an embodiment of the present invention mainly includes a binder resin as matrix particles for the toner, a charge control agent for controlling charging properties of the toner, and a coloring agent. Hereinafter, the respective components for the toner according to the present invention will be described.

[Binder Resin]

The toner according to the present invention uses the binder resin as the matrix particles for supporting the components of the toner such as the charge control agent and the coloring agent.

Non-limiting examples of the binder resin include styrene-acrylate based copolymer resin or polyester based polymer resin, but any known one may be used. Specific examples include a vinyl polymer of a styrene based monomer, an acrylate based monomer, a methacrylate based monomer, etc.; a copolymer of two or more of these monomers; a polyester based polymer; polyol resin; phenol resin; silicone resin; polyurethane resin; polyamide resin; furan resin; epoxy resin; xylene resin; terpene resin; coumarone-indene resin; polycarbonate resin; petroleum based resin; or the like.

Examples of the styrene based monomer include styrene, o-methyl styrene, m-methyl styrene, p-methyl styrene, p-phenyl styrene, p-ethyl styrene, 2,4-dimethyl styrene, p-n-amyl styrene, p-tert-butyl styrene, p-n-hexyl styrene, p-n-octyl styrene, p-n-nonyl styrene, p-n-decyl styrene, p-n-dodecyl styrene, p-methoxy styrene, p-chlor styrene, 3,4-dichloro styrene, m-nitro styrene, o-nitro styrene and p-nitro styrene, and a derivative thereof.

Examples of the acrylate based monomer include acrylic acid or an acrylate ester such as methyl acrylate, ethyl acrylate, propyl acrylate, n-butyl acrylate, isobutyl acrylate, n-octyl acrylate, n-dodecyl acrylate, 2-ethylhexyl acrylate, stearyl acrylate, 2-chlorethyl acrylate and phenyl acrylate.

Examples of the methacrylate based monomer include methacrylic acid or a methacrylate ester such as methyl methacrylate, ethyl methacrylate, propyl methacrylate, n-butyl methacrylate, isobutyl methacrylate, n-octyl methacrylate, n-dodecyl methacrylate, 2-ethylhexyl methacrylate, stearyl methacrylate, phenyl methacrylate, dimethylaminoethyl methacrylate and diethylaminoethyl methacrylate.

Examples of other monomers forming the vinyl polymer resin or the vinyl copolymer resin include monoolefins; polyenes; vinyl halides; vinyl esters; vinyl ethers; vinyl ketons; an N-vinyl compound; vinyl naphthalenes; a monomer having a carboxyl group including the following such as an acid anhydride, a monoester of acrylate or methacrylate derivatives etc., an unsaturated dibasic acid anhydride, a monoester of an unsaturated dibasic acid, an unsaturated dibasic acid ester, an $\alpha,\beta$-unsaturated acid, an $\alpha,\beta$-unsaturated acid anhydride, a mixed acid anhydride of an $\alpha,\beta$-unsaturated acid and a lower aliphatic acid; a monomer having a carboxyl group including an acid anhydride and a monoester of alkenyl malonate, alkenyl glutarate, and alkenyl adipate; acrylic acid hydroxyalkyl esters; a monomer having a hydroxyl group such as 4-(1-hydroxy-1-methylbutyl)styrene, 4-(1-hydroxy-1-methylhexyl)styrene etc.

The vinyl polymer resin or the vinyl copolymer resin may be cross-linked by a cross-linking agent having two or more vinyl groups. Examples of the cross-linking agent include an aromatic divinyl compound such as divinylbenzene and divinylnaphthalene; a diacrylate compound such as neopentyl glycol diacrylate or a corresponding dimethacrylate compound; and a diacrylate compound of alkylene diol or a corresponding dimethacrylate compound.

Examples of other cross-linking agents include a diacrylate compound bonded by a chain including an aromatic group and an ether bond or a corresponding dimethacrylate compound and polyester type diacrylate (a trade name of MANDA manufactured by Nippon Kayaku Co., Ltd.).

In addition, examples of a polyfunctional cross-linking agent include an acrylate compound such as pentaerythritol triacrylate, trimethylolethan triacrylate, trimethylolpropane triacylate, tetramethylolmethane tetraacrylate and oligoester acrylate, or a corresponding methacrylate compound, triallyl cyanurate and triallyl trimellitate.

Preferably 0.01 to 10 parts by mass, more preferably 0.03 to 5 parts by mass of the cross-linking agent is used based on 100 parts by mass of other monomer components. Among the cross-linking agents, an aromatic divinyl compound (especially, divinylbenzene) and diacrylate compounds bonded by a bonding chain including one aromatic group and one ether group are suitably used in resin for toner from the viewpoint of fixability and offset resistance. Among them, a monomer combination for forming a styrene based copolymer or a styrene-acrylate based copolymer is preferable.

As a polymerization initiator used in the manufacture of the vinyl copolymer resin or the vinyl copolymer resin, known one may be used. Specific examples include an azo compound such as 2,2'-azobisisobutyronitrile and an organic peroxide such as methylethylketone peroxide.

The monomer for the polyester based polymer resin is as follows:

Examples of a divalent alcohol include ethylene glycol, propylene glycol, 1,3-butane diol, 1,4-butane diol, 2,3-butane diol, diethylene glycol, triethylene glycol, 1,5-pentanediol, 1,6-hexanediol, neopentyl glycol, 2-ethyl-1,3-hexanediol, hydrogenated bisphenol A and diols obtained by polymerizing bisphenol A with cyclic ethers such as ethylene oxide and propylene oxide.

In order to cross-link the polyester based polymer resin, polyvalent, e.g., trivalent or more, alcohol is used together as a monomer. Examples of the polyvalent, e.g., trivalent or more, alcohol include sorbitol, 1,2,3,6-hexane tetrol, 1,4-sorbitan, pentaerythritol, dipentaerythritol, tripentaerythritol, 1,2,4-butanetriol, 1,2,5-pentatriol, glycerol, 2-methylpropanetriol, 2-methyl-1,2,4-butanetriol, trimethylol ethane, trimethylol propane and 1,3,5-trihydroxy benzene.

Examples of acid for forming the polyester based polymer resin include benzene dicarboxylic acid or anhydride thereof, alkyl dicarboxylic acid or anhydride thereof, and unsaturated dibasic acid or anhydride thereof. Examples of polyvalent, e.g., trivalent or more, carboxylic acid include trimellitic acid, pyromellitic acid, 2,5,7-naphthalene tricarboxylic acid, 1,2,4-naphthalene tricarboxylic acid, 1,2,4-butane tricarboxylic acid, 1,2,5-hexane tricarboxylic acid, 1,3-dicarboxy-2-methyl-2-methylene carboxypropane, tetra (methylenecarboxy)methane, 1,2,7,8-octane tetra carboxylic acid, a trimer acid or an anhydride thereof and a part lower alkyl ester.

As the binder resin, a mixture of two types or more of amorphous polyester polymer resin and crystal polyester polymer resin may be used. In this case, the materials may be preferably selected by taking its compatibility into account. The amorphous polyester polymer resin may be synthesized from polyvalent carboxylic acid components, preferably from aromatic polyvalent carboxylic acid and polyvalent alcohol components. The crystal polyester polymer resin may be synthesized from divalent carboxylic acid components, preferably from aliphatic dicarboxylic acid and divalent alcohol components.

The binder resin may include a vinyl polymer resin component and/or a polyester based polymer resin component, and a monomer component that may react with these both resin components. Examples of the monomer of the polyester based polymer resin component that may react with the vinyl polymer include unsaturated dicarboxylic acid such as phthalic acid, maleic acid, citraconic acid and itaconic acid or anhydride thereof. Examples of the monomer of the vinyl polymer resin component include those having a carboxyl group or a hydroxy group, acrylic acid or methacrylic acid esters. If the polyester based polymer resin, the vinyl polymer resin and other binder resin are used in combination, it preferably includes 60% by mass or more of resin having an acid value of 0.1 to 50 mgKOH/g in respect to the whole binder resin.

The binder resin and the composition including the binder resin each has a glass transfer temperature (Tg) of preferably 35 to 80° C., more preferably 40 to 75° C. from the viewpoint of toner storage stability. If Tg is 35° C. or more, the toner can be prevented from degrading under high temperature atmosphere, and offset upon fixing can be inhibited. If Tg is 80° C. or less, the fixability becomes better.

In the polymerized toner (chemical toner) according to the present embodiment, the binder resin having a softening point of 80 to 140° C. is suitably used. If the softening point of the binder resin is 80° C. or more, a condition of the toner after fixing and during storage and an image stability of the toner will be better. If the softening point is 140° C. or less, fixability at low temperature will be better.

[Charge Control Agent]

The toner according to the present embodiment contains a charge control agent. The charge control agent is used for the purpose of controlling charging properties of the toner, and attaching the toner stably on an electrostatic latent image formed on a photoreceptor. Hereinafter, the charge transfer agent according to the present embodiment will be described in detail.

The charge control agent according to the present embodiment (hereinafter referred to as a charge control agent A) includes a bisphthalimide derivative represented by the formula (1). Firstly, the bisphthalimide derivative represented by the formula (1) will be described.

[Chemical Formula 4]

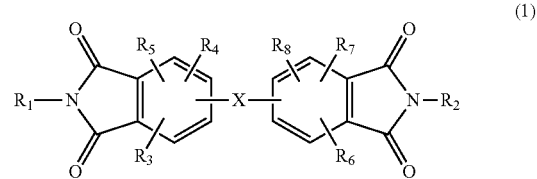

(1)

In the formula (1), X represents a carbonyl group, a sulfur atom, a sulfinyl group, a sulfonyl group or a single bond. If X is a single bond, one phthalimide is directly bonded to the other phthalimide on any carbon on a benzene ring of phthalimide. X in the formula (1) is bonded to any of carbons on the benzene ring of phthalimide, and is preferably bonded at a position shown in the formula (2). Preferably, X is a carbonyl group, a sulfinyl group or a single bond.

[Chemical Formula 5]

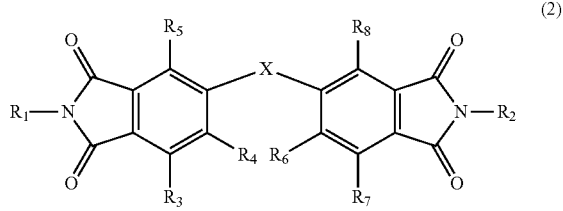

(2)

In the formula (1), $R_1$ and $R_2$ each represents a linear or branched alkyl group having 1 to 20 carbon atoms, a cycloalkyl group having 5 to 10 carbon atoms, an aromatic hydrocarbon group, a heterocyclic group or a fused polycyclic aromatic hydrocarbon. $R_1$ and $R_2$ each may have a substituent.

In the formula (1), $R_1$ and $R_2$ each is preferably a linear or branched alkyl group having 1 to 20 carbon atoms, a cycloalkyl group having 5 to 10 carbon atoms, an aromatic hydrocarbon group or a heterocyclic group, more preferably a linear or branched alkyl group having 1 to 10 carbon atoms, a cycloalkyl group having 5 to 8 carbon atoms or an aromatic hydrocarbon group. In this case, a substituent that the aromatic hydrocarbon group may have is preferably a trifluoromethyl group, a cyano group, a nitro group, a hydroxyl group; a halogen atom such as a fluorine atom, a chlorine atom, a bromine atom and an iodine atom; a linear or branched alkyl group having 1 to 8 carbon atoms such as a methyl group, an ethyl group, an n-propyl group, an isopropyl group, an n-butyl group, an isobutyl group, a tert-butyl group, an n-pentyl group, an isopentyl group, a neopentyl group, an n-hexyl group, an n-heptyl group, an isoheptyl group, an n-octyl group and an isooctyl group; and a linear or branched alkyloxy group having 1 to 8 carbon atoms such as a methyloxy group, an ethyloxy group and a propyloxy group.

Examples of the "linear or branched alkyl group having 1 to 20 carbon atoms" or the "cycloalkyl group having 5 to 10 carbon atoms" represented by $R_1$ and $R_2$ in the formula (1) include an alkyl group such as a methyl group, an ethyl group, an n-propyl group, a 2-propyl group, an n-butyl group, a sec-butyl group, a 2-methyl propyl group, a tert-butyl group, an n-pentyl group, a 1-methylbutyl group, a 1-ethylpropyl group, a 1,1-dimethylpropyl group, 1,2-dimethylpropyl group, an n-hexyl group, a 1-methylpentyl group, 2-methylpentyl group, 3-methylpentyl group, 4-methylpentyl group, 1-ethylbutyl group, 2-ethylbutyl group, 1,1-dimethylbutyl group, 1,2-dimethylbuthyl group, 1,3-dimethylbuthyl group, 1,4-dimethylbuthyl group, 2,2-dimethylbuthyl group, 2,3-dimethylbuthyl group, 3,3-dimethylbuthyl group, 1-ethyl-2-methyl-propyl group, 1,1,2-trimethylpropyl group, n-heptyl group, 2-methylhexyl group, n-octyl group, an isooctyl group, a tert-octyl group, a 2-ethylhexyl group, a 3-methylheptyl group, an n-nonyl group, an isononyl group, a 1-methyloctyl group, a 2-ethylheptyl group, an n-decyl group, a 1-methylnonyl group, an n-undecyl group, 1,1-dimethylnonyl group, an n-dodecyl group, an n-tetradecyl group, an n-heptadecyl group and an n-octadecyl group; and a cycloalkyl group such as a cyclopentyl group, a cyclohexyl group, a 1-adamantyl group and a 2-adamantyl group.

Examples of the substituent that the "linear or branched alkyl group having 1 to 20 carbon atoms" or the "cycloalkyl group having 5 to 10 carbon atoms" represented by $R_1$ and $R_2$ in the formula (1) may have include a deuterium atom; a halogen atom such as a fluorine atom, a chlorine atom, a bromine atom and an iodine atom; a functional group such as a trifluoromethyl group, a cyano group, a nitro group and a hydroxyl group; a linear or branched alkyl group having 1 to 8 carbon atoms such as a methyl group, an ethyl group, an n-propyl group, an isopropyl group, an n-butyl group, an isobutyl group, a tert-butyl group, an n-pentyl group, an isopentyl group, a neopentyl group, an n-hexyl group, an n-heptyl group, an isoheptyl group, an n-octyl group and an isooctyl group; a linear or branched alkyloxy group having 1 to 8 carbon atoms such as a methyloxy group, an ethyloxy group and a propyloxy group; an alkenyl group such as allyl group; an aralkyl group such as a benzyl group, a naphthylmethyl group and a phenethyl group; an aryloxy group such as a phenyloxy group and a tolyloxy group; an arylalkyloxy group such as benzyloxy group and a phenethyloxy group; an aromatic hydrocarbon group or a fused polycyclic aromatic hydrocarbon such as a phenyl group, a biphenyl group, a terphenlyl group, a naphthyl group, an anthracenyl group, a phenanthryl group, a fluorenyl group, an indenyl group, a pyrenyl group, a perylenyl group, a fluoranthenyl group and a triphenylenyl group; a heterocyclic group such as a pyridyl group, a pyranyl group, a thienyl group, a furyl group, a pyrrolyl group, a pyrrolidinyl group, an imidazolyl group, an imidazolidinyl group, a pyrazolyl group, pyrazolidinyl group, a pyridazinyl group, a pyrazinyl group, a piperidinyl group, piperadinyl group, a thiolanyl group, a thianyl group, a quinolyl group, an isoquinolyl group, a benzofuranyl group, a benzothienyl group, an indolyl group, a carbazolyl group, a benzooxazolyl group, a benzothiazolyl group, a quinoxalyl group, a benzoimidazolyl group, a dibenzofuranyl group, a dibenzothienyl group and a carbolynyl group; an aryl vinyl group such as a stylyl group and a naphthyl vinyl group; an acyl group such as an acetyl group and a benzoyl group; a dialkylamino group such as a dimethylamino group and a dinaphthylamino group; a disubstituted amino group substituted with an aromatic hydrocarbon group or a fused polycyclic aromatic hydrocarbon such as a diphenylamino group and a dinaphthylamino group; a diaralkylamino group such as a dibenzylamino group and a diphenetylamino group; a disubstituted amino group substituted with a heterocyclic group such as a dipyridylamino group, dithienylamino group and dipiperidinylamino group; a dialkenylamino group such as a diallylamino group; and a disubstituted amino group that is substituted with a group selected from an alkyl group, an aromatic hydrocarbon group, a fused polycyclic aromatic hydrocarbon, an aralkyl group, a heterocyclic group and an alkenyl group. These substituents may have other substituents listed above, and may form a ring by bonding each other via a single bond, an oxygen atom or a sulfur atom.

Examples of the "aromatic hydrocarbon group", the "heterocyclic group" or the "fused polycyclic aromatic hydrocarbon" represented by $R_1$ and $R_2$ in the formula (1) include a phenyl group, a biphenylyl group, a terphenlyl group, a naphthyl group, an anthryl group, a phenanthryl group, a fluorenyl group, an indenyl group, a pyrenyl group, a perylenyl group, a fluoranthenyl group and a triphenylenyl group, a pyridyl group, a furyl group, a pyranyl group, a thienyl group, a pyrrolidinyl group, an imidazolyl group, an imidazolidinyl group, a pyrazolyl group, pyrazolidinyl group, a pyridazinyl group, a pyrazinyl group, a piperidinyl group, piperadinyl group, a thiolanyl group, a thianyl group, a quinolyl group, an isoquinolyl group, a benzofuranyl group, a benzothienyl group, an indolyl group, a carbazolyl group, a benzooxazolyl group, a benzothiazolyl group, a quinoxalyl group, a benzoimidazolyl group, a dibenzofuranyl group, a dibenzothienyl group and a carbolynyl group.

The substituents that the "aromatic hydrocarbon group", the "heterocyclic group" or the "fused polycyclic aromatic hydrocarbon" represented by $R_1$ and $R_2$ in the formula (1) may have, may be similar to those listed as the substituents that the "linear or branched alkyl group having 1 to 20 carbon atoms" or the "cycloalkyl group having 5 to 10 carbon atoms" represented by $R_1$ and $R_2$ in the formula (1) may have. The possible embodiments may be similar.

$R_3$ to $R_8$ in the formula (1) each represents a hydrogen atom, a deuterium atom, a halogen atom, a hydroxyl group, a cyano group, a trifluoromethyl group, a nitro group, a linear or branched alkyl group having 1 to 20 carbon atoms, a cycloalkyl group having 5 to 10 carbon atoms, a linear or branched alkenyl group having 2 to 6 carbon atoms, a linear or branched alkyloxy group having 1 to 8 carbon atoms, a cycloalkyloxy group having 5 to 10 carbon atoms, an aromatic hydrocarbon group, a heterocyclic group, a fused polycyclic aromatic hydrocarbon or an aryloxy group. Note that $R_3$ to $R_8$ each may have a substituent.

Preferably, $R_3$ to $R_8$ in the formula (1) each is a hydrogen atom, a deuterium atom, a halogen atom, a hydroxyl group, a cyano group, a trifluoromethyl group, a nitro group, a linear or branched alkyl group having 1 to 20 carbon atoms, a cycloalkyl group having 5 to 10 carbon atoms, a linear or branched alkenyl group having 2 to 6 carbon atoms, a linear or branched alkyloxy group having 1 to 8 carbon atoms, or an aromatic hydrocarbon group.

More preferably, $R_3$ to $R_8$ in the formula (1) each is a hydrogen atom, a deuterium atom, a halogen atom, a hydroxyl group, a cyano group, a trifluoromethyl group, a nitro group, a linear or branched alkyl group having 1 to 10 carbon atoms, a cycloalkyl group having 5 to 8 carbon atoms, or a linear or branched alkenyl group having 2 to 6 carbon atoms. Most preferably, that is a hydrogen atom or a deuterium atom.

Examples of the "halogen atom" represented by $R_3$ to $R_8$ in the formula (1) include a fluorine atom, a chlorine atom, a bromine atom and an iodine atom.

The "linear or branched alkyl group having 1 to 20 carbon atoms" or the "cycloalkyl group having 5 to 10 carbon atoms" represented by $R_3$ to $R_8$ in the formula (1) may be similar to those listed as the "linear or branched alkyl group having 1 to 20 carbon atoms" or the "cycloalkyl group having 5 to 10 carbon atoms" represented by $R_1$ and $R_2$ in the formula (1). The possible embodiments may be similar.

Examples of the "linear or branched alkenyl group having 2 to 6 carbon atoms" represented by $R_3$ to $R_8$ in the formula (1) include a vinyl group, an allyl group, an isopropenyl group and 2-butenyl group.

Examples of the "linear or branched alkyloxy group having 1 to 8 carbon atoms" or the "cycloalkyl group having 5 to 10 carbon atoms" represented by $R_3$ to $R_8$ in the formula (1) include an alkyloxy group such as a methyloxy group, an ethyloxy group, an n-propyloxy group, an isopropyloxy group, an n-butyloxy group, a tert-butyloxy group, an n-pentyloxy group, an n-hexyloxy group, an n-heptyloxy group, an isoheptyloxy group, an n-octyloxy group, an isooctyloxy group; and a cycloalkyloxy group such as a cyclopentyloxy group, a cyclohexyloxy group, a cycloheptyloxy group, a cyclooctyloxy group, a 1-adamantyloxy group and 2-adamantyloxy group.

The substituents that the "linear or branched alkyl group having 1 to 20 carbon atoms", the "cycloalkyl group having 5 to 10 carbon atoms", the "linear or branched alkenyl group having 2 to 6 carbon atoms", the "linear or branched alkyloxy group having 1 to 8 carbon atoms" or the "cycloalkyloxy group having 5 to 10 carbon atoms" represented by $R_3$ to $R_8$ in the formula (1) may have, may be similar to those listed as the substituents that the "linear or branched alkyl group having 1 to 20 carbon atoms" or the "cycloalkyl group having 5 to 10 carbon atoms" represented by $R_1$ and $R_2$ in the formula (1) may have. The possible embodiments may be similar.

The "aromatic hydrocarbon group", the "heterocyclic group" or the "fused polycyclic aromatic hydrocarbon" represented by $R_3$ to $R_8$ in the formula (1) may be similar to those listed as the "aromatic hydrocarbon group", the "heterocyclic group" or the "fused polycyclic aromatic hydrocarbon" represented by $R_1$ and $R_2$ in the formula (1). The possible embodiments may be similar.

Examples of the "aryloxyl group" represented by $R_3$ to $R_8$ in the formula (1) include a phenyloxy group, a tolyloxy group, a biphenyloxy group, a terphenlyloxy group, a naphthyloxy group, an anthracenyloxy group, a phenanthryloxy group, a fluorenyloxy group, an indenyloxy group, a pyrenyloxy group and a perylenyloxy group.

The substituents that "aromatic hydrocarbon group", the "heterocyclic group", the "fused polycyclic aromatic hydrocarbon" or the "aryloxy group" represented by $R_3$ to $R_8$ in the formula (1) may have, may be similar to those listed as the substituents that the "linear or branched alkyl group having 1 to 20 carbon atoms" or the "cycloalkyl group having 5 to 10 carbon atoms" represented by $R_1$ and $R_2$ in the formula (1) may have. The possible embodiments may be similar.

$R_3$ to $R_5$ and $R_6$ to $R_8$ in the formula (1) may bond each other to form a ring. In this case, the ring is preferably formed via a single bond, an oxygen atom or a sulfur atom. $R_3$ to $R_8$ in the formula (1) is bonded to any of carbons on the benzene ring of phthalimide, and is preferably bonded at a position shown in the formula (2). In this case, $R_3$ and $R_4$, and $R_6$ and $R_7$ may bond each other to form a ring.

The bisphthalimide derivative represented by the formula (1) may be produced by a known method. For example, a dimer of phthalic anhydrides where phthalic anhydrides such as benzophenone dicarboxylic anhydrides each having a corresponding substituent are bonded via a carbonyl group, a sulfur atom, a sulfinyl group or a sulfonyl group is condensation-reacted with an aromatic hydrocarbon or a fused polycyclic aromatic having an amino group such as aniline having a corresponding substituent in the presence of chlorine, thereby synthesizing the bisphthalimide derivative used in the present invention.

Among the bisphthalimide derivatives represented by the formula (1), illustrative preferable compounds are shown in the following chemical formulae (3) to (52) (referred to as compounds 3 to 52), but the present invention is not limited to the compounds. Note that in the following structural chemical formulae hydrogen atoms are partly omitted. In addition, even if stereoisomers may exist, planar structural chemical formulae are shown.

[Chemical formula 6]

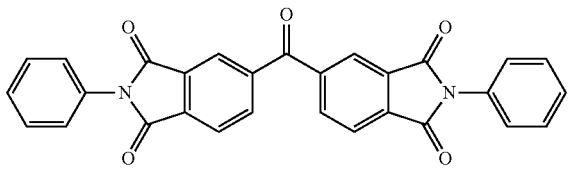

(3)

[Chemical formula 7]

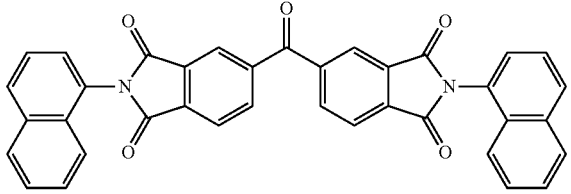

(4)

[Chemical formula 8]

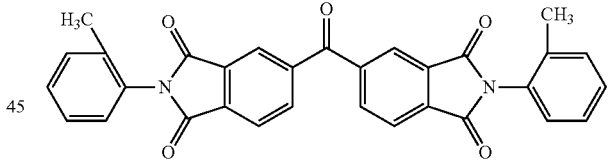

(5)

[Chemical formula 9]

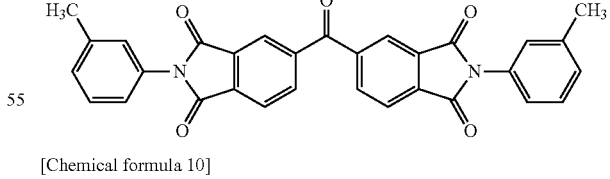

(6)

[Chemical formula 10]

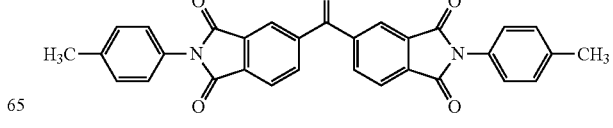

(7)

[Chemical formula 11]
(8)
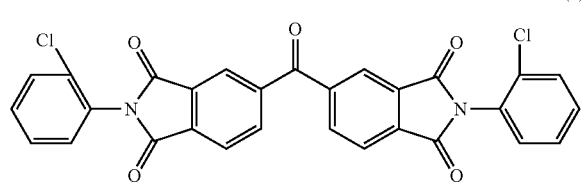
[Chemical formula 12]
(9)
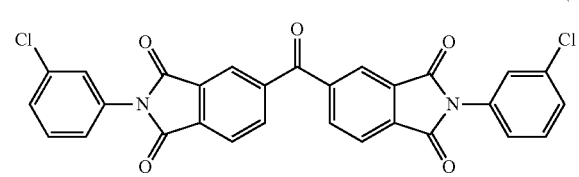
[Chemical formula 13]
(10)
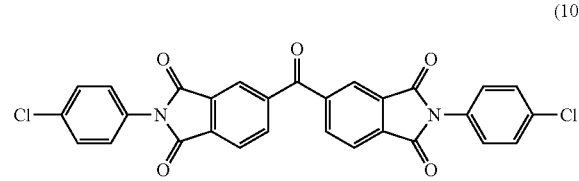
[Chemical formula 14]
(11)
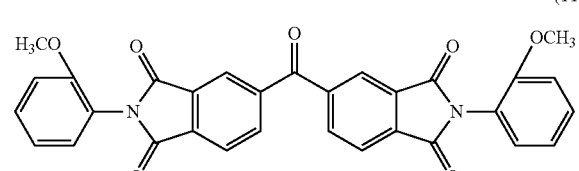
[Chemical formula 15]
(12)
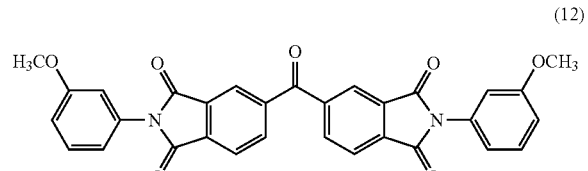
[Chemical formula 16]
(13)
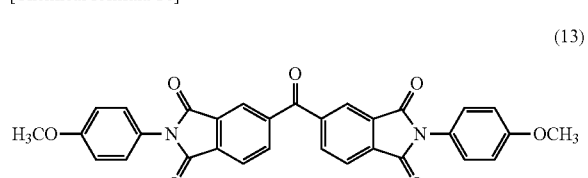
[Chemical formula 17]
(14)
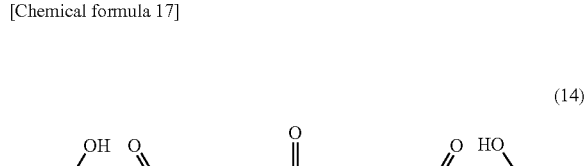
[Chemical formula 18]
(15)
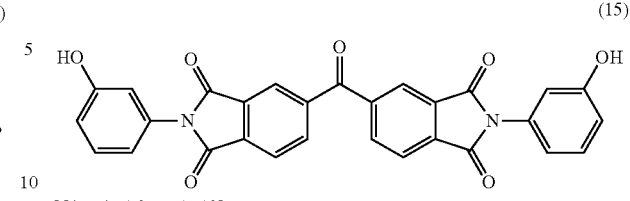
[Chemical formula 19]
(16)
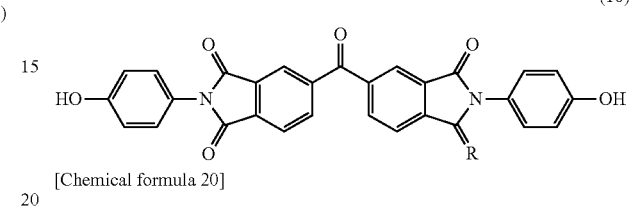
[Chemical formula 20]
(17)
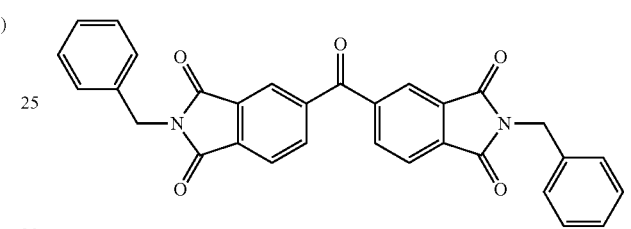
[Chemical formula 21]
(18)
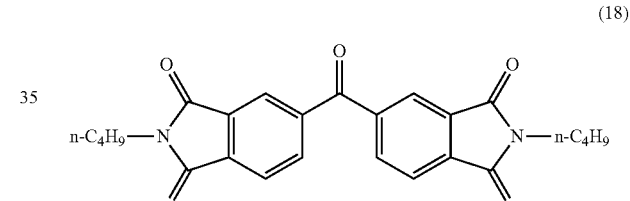
[Chemical formula 22]
(19)
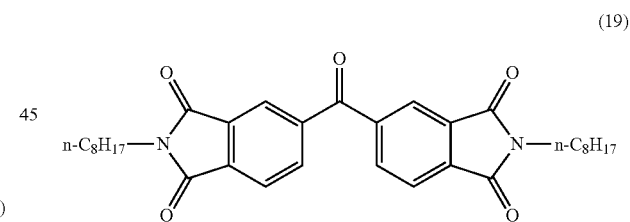
[Chemical formula 23]
(20)
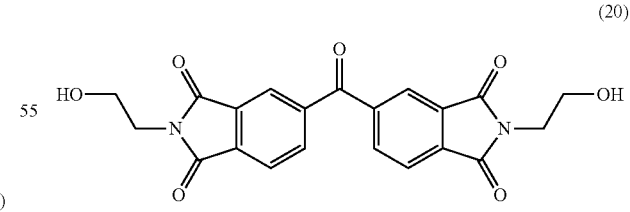
[Chemical formula 24]
(21)
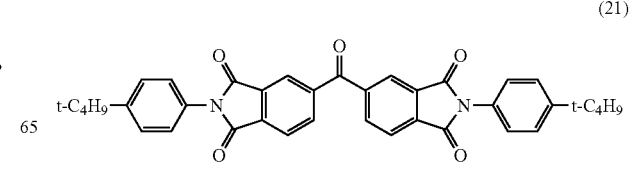

[Chemical formula 25]
(22)
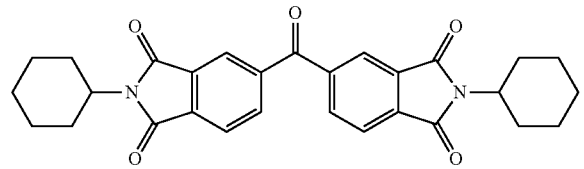
[Chemical formula 26]
(23)
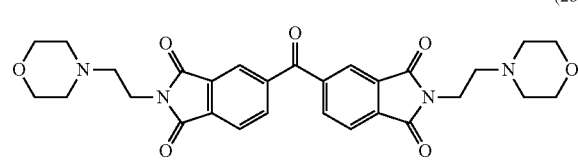
[Chemical formula 27]
(24)
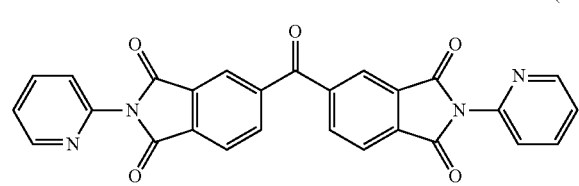
[Chemical formula 28]
(25)
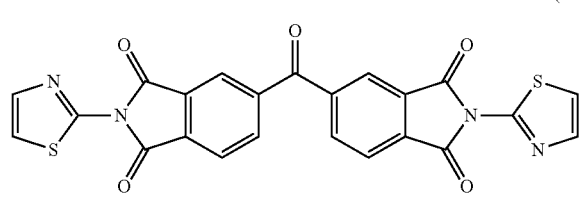
[Chemical formula 29]
(26)
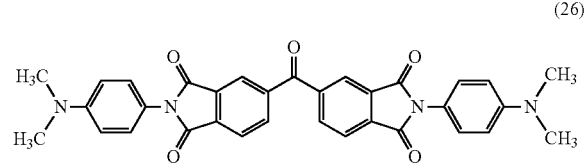
[Chemical formula 30]
(27)
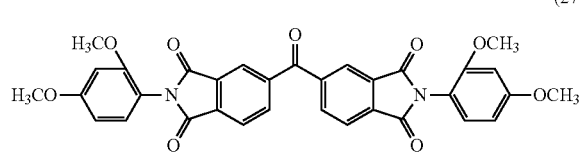
[Chemical formula 31]
(28)
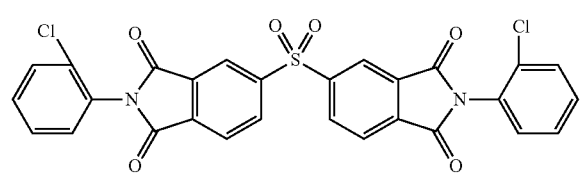
[Chemical formula 32]
(29)
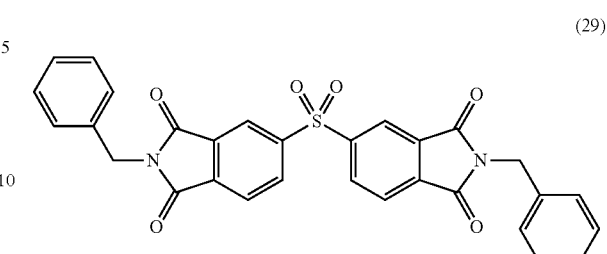
[Chemical formula 33]
(30)
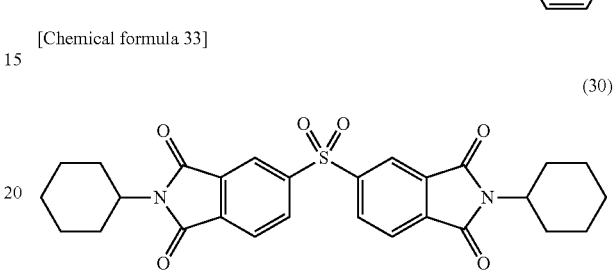
[Chemical formula 34]
(31)
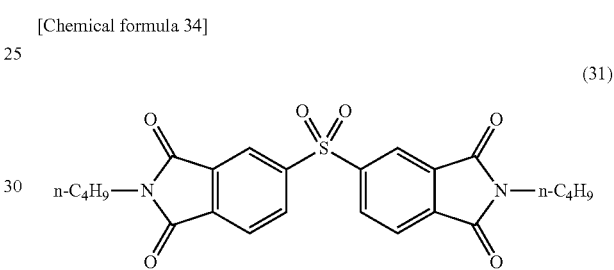
[Chemical formula 35]
(32)
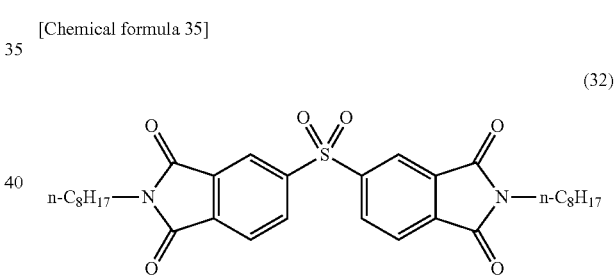
[Chemical formula 36]
(33)
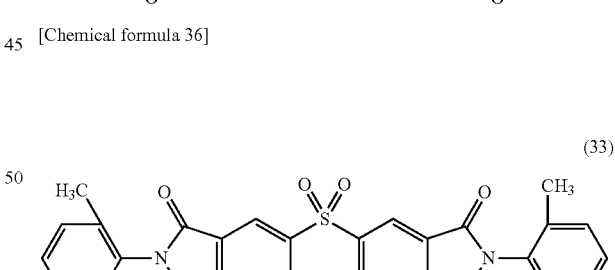
[Chemical formula 37]
(34)
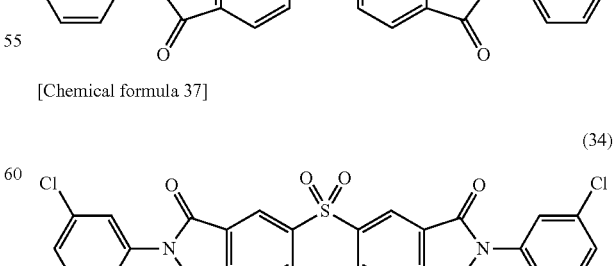

[Chemical formula 38] (35)

[Chemical formula 39] (36)

[Chemical formula 40] (37)

[Chemical formula 41] (38)

[Chemical formula 42] (39)

[Chemical formula 43] (40)

[Chemical formula 44] (41)

[Chemical formula 45] (42)

[Chemical formula 46] (43)

[Chemical formula 47] (44)

[Chemical formula 48] (45)

[Chemical formula 49] (46)

[Chemical formula 50] (47)

[Chemical formula 51] (48)

-continued

[Chemical formula 52]

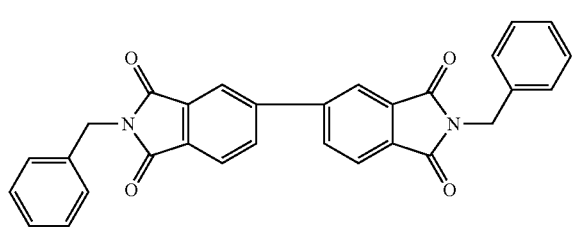

(49)

[Chemical formula 53]

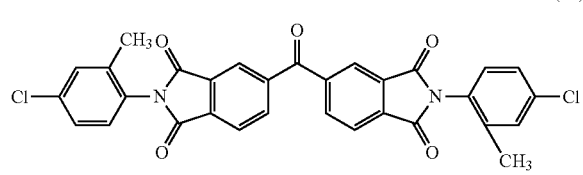

(50)

[Chemical formula 54]

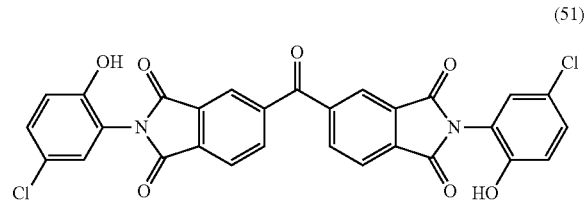

(51)

[Chemical formula 55]

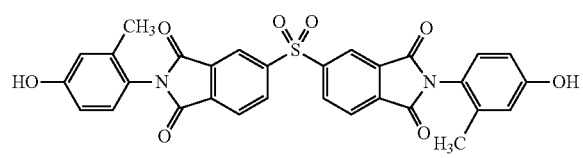

(52)

The charge control agent A includes the bisphthalimide derivative represented by the formula (1), and therefore has especially excellent charging properties including a high charge rise speed, a high charge amount and environmental stability as compared with the charge control agent in the related art. In addition, as the charge control agent contains no heavy metals, a less burden is applied to human and environment, and dispersibility and a compound stability are excellent.

The charge control agent A is preferably used by adjusting a volume average particle size to 0.1 to 20 μm, more preferably 0.1 to 10 μm.

By adjusting the volume average particle size of the charge control agent A to 0.1 μm or more, the charge control agent A appears easily on the surface of the toner. In this manner, an intended charge control effect may be provided. Also, by adjusting the volume average particle size of the charge control agent A to 20 μm or less, the charge control agent A dropping off from the toner may be reduced. In this way, an adverse effect such as contamination in-machine may be prevented.

Using a known method, the charge control agent A may be added. Specifically, the charge control agent A is added to binder resin together with a coloring agent to be kneaded and pulverized (pulverization method). Alternatively, the charge control agent A is added to a polymerizable monomer to be polymerized, thereby providing a toner (polymerization method). In this way, the charge control agent A is added in advance inside of toner particles (internal addition), or is added on surfaces of toner particles produced (external addition).

When the charge control agent A is internally added to the toner particles, an addition amount is preferably 0.1 to 10 parts by mass, more preferably 0.2 to 5 parts by mass based on 100 parts by mass of the binder resin. On the other hand, when the charge control agent A is externally added to the toner particles, an addition amount is preferably 0.01 to 5 parts by mass, more preferably 0.01 to 2 parts by mass based on 100 parts by mass of the binder resin. It is more preferable that the charge control agent A be fixed mechanochemically to the surfaces of the toner particles.

When the charge control agent A is used for polymerized toner, the volume average particle size is preferably adjusted to 1.0 μm or less, more preferably 0.01 to 1.0 μm. If the volume average particle size of the charge control agent A is within the above-described range, the charge control agent A is less unevenly distributed in the toner and is well dispersed in the toner, and the variation of performance and reliability is reduced.

The charge control agent A may be used in combination with other known negative chargeable charge control agents. Examples of such other charge control agents include an azo based iron complex or its complex salt, an azo based chromium complex or its complex salt, an azo based manganese complex or its complex salt, an azo based cobalt complex or its complex salt, an azo based zirconium complex or its complex salt, a chromium complex of a carboxylic acid derivative or its complex salt, a zinc complex of a carboxylic acid derivative or its complex salt, an aluminum complex of a carboxylic acid derivative or its complex salt and a zirconium complex of a carboxylic acid derivative or its complex salt. As the carboxylic acid derivative, aromatic hydroxy carboxylic acid is preferable, and 3,5-di-tert-butyl-salicylic acid is more preferable. Further examples of negative chargeable resin type charge control agents include a boron complex or its complex salt.

If the charge control agent A is used in combination with other known charge control agents, the addition amount of the other charge control agents is preferably 0.1 to 10 parts by mass based on 100 parts by mass of the binder resin.

The charge control agent A is also suitable as a charge control agent (charge enhancer) in a coating agent for an electrostatic powder coating. In other words, the coating agent for the electrostatic powder coating using a charge enhancer has excellent environment resistance and storage stability, especially thermal stability and durability, has a coating efficiency of 100%, and can form a thick film with no coating defect.

[Coloring Agent]

As a coloring agent included in the toner according to the present embodiment, known one may be used. For example, the following coloring agents may be used, but are not limited thereto.

As a black toner, the following color agents may be used. Examples include black or blue dye such as azo based dye, anthraquinone based dye, xanthene based dye and methine based dye; or a black or blue pigment such as carbon black, aniline black, acetylene black, phthalocyanine blue and indanthrene blue.

As a color toner, the following color agents may be used. As a magenta coloring agent, examples include a condensed azo compound, a diketo pyrrolo-pyrrole compound, an anthraquinone compound, a quinacridone compound, basic dye, lake dye, naphthol dye, a benzimidazolone compound, a thioindigo compound and a perylene compound.

As a pigment based magenta coloring agent, examples include C.I. Pigment Red, C.I. Pigment Violet and C.I. Vat Red. The pigment may be used alone, but may be preferably used in combination with dye from the viewpoint of increasing of an image quality/clearness.

As a dye based magenta coloring agent, examples include oil soluble dye such as C.I. Solvent Red, C.I. Disperse Red, C.I. Solvent Violet and C.I. Disperse Violet, and basic dye such as C.I. Basic Red and C.I. Basic Violet.

As a cyan coloring agent, a copper phthalocyanine compound and its derivative thereof, anthraquinone or a based dye lake compound may be used, for example.

As a yellow coloring agent, a fused azo compound, an isoindolinone compound, an anthraquinone compound, an azo metal complex, a methine compound or an arylamide compound may be used, for example.

As an orange pigment, examples include Red Chrome Yellow, Molybdenum Orange, Permanent Orange GTR, Pyrazolone Orange, Vulcan Orange, Benzidine Orange G, Indanthrene Brilliant Orange RK and Indanthrene Brilliant Orange GK. As a violet pigment, examples include Manganese Violet, Fast Violet B and Methyl Violet Lake. As a green pigment, chromium oxide, Chromium Green, Pigment Green, Malachite Green Lake and Final Yellow Green G. As a white pigment, examples include zinc oxide, titanium oxide, antimony white and zinc sulfide.

An amount of each coloring agent described above is preferably 0.1 to 20 parts by mass based on 100 parts by mass of the binder resin.

[Additives]

To the toner according to the present embodiment, a variety of additives may be added in order to provide desirable physical properties. As the additives, wax, a flow improver and a magnetic material may be mainly used.

(1) Wax

Wax (a releasing agent) is added in order to prevent offset upon fixing and improve paper feeding properties. Examples of wax include aliphatic hydrocarbon based wax, an oxide or a block copolymer of aliphatic hydrocarbon based wax, vegetable based wax, animal based wax, mineral based wax, wax mainly containing fatty acid ester and fatty acid ester of which part or all is deoxidized.

By using two or more types of wax in combination, a plasticization action and a releasing action may be exercised at the same time as the action of wax. Examples of the wax having the plasticization action include wax having a low melting point, a branched structure or a polar group. Examples of the wax having the releasing action include wax having a high melting point, a linear chain structure, or being non-polar having no functional group. As application examples, a combination of two or more types of wax having a difference between melting points being 10° C. to 100° C., a combination of polyolefin and graft modified polyolefin, and so on may be listed.

The melting point of the wax is preferably 50 to 140° C., more preferably 70 to 120° C. to balance fixability with offset resistance. When the melting point is 50° C. or more, blocking resistance may be improved. When the melting point is 140° C. or less, offset resistance may be easily exercised.

A total amount of the wax is preferably 0.2 to 20 parts by mass, more preferably 0.5 to 10 parts by mass based on 100 parts by mass of the binder resin.

(2) Flow Improver

A flow improver is an additive for improving flowability of the toner (flowing easily), and is added on the surface of the toner. Examples of the flow improver include carbon black, vinylidene fluoride fine powder, fluorine based resin powder such as polytetrafluoroethylene fine powder, fine powder silica such as wet process silica, fine powder titanium oxide, or fine powder alumina; and treated silica, treated titanium oxide and treated alumina that are provided by surface-treating the former with a silane coupling agent, a titanium coupling agent or silicone oil. Among them, fine powder silica, fine powder titanium oxide and fine powder alumina are preferable. More preferable is treated silica that is surface-treated with a silane coupling agent or the like.

The flow improver has an average particle size of preferably 0.001 to 2 μm, more preferably 0.002 to 0.2 μm. A number average particle size thereof is preferably 5 to 100 nm, more preferably 5 to 50 nm. A nitrogen adsorption specific surface area thereof measured by a BET method is preferably 30 m$^2$/g or more, more preferably 60 to 400 m$^2$/g. The same of the fine powder surface-treated is preferably 20 m$^2$/g or more, more preferably 40 to 300 m$^2$/g. An amount used of the fine powder is preferably 0.03 to 8 parts by mass based on 100 parts by mass of the toner particles.

(3) Magnetic Material

The magnetic material is added for providing the toner with magnetism. Examples of the magnetic material include a magnetic iron oxide such as magnetite, maghemite and ferrite and an iron oxide including other metal oxide; a metal such as iron, cobalt and nickel; or an alloy of the aforementioned metal and an metal such as aluminum, cobalt, copper, lead, magnesium, tin, zinc, antimony, beryllium, bismuth, cadmium, calcium, manganese, selenium, titanium, tungsten and vanadium. It may be used alone or in combination of two or more thereof.

Also, as the magnetic material, magnetic iron oxide such as magnetite, maghemite and ferrite including different kind elements or a mixture thereof may be used. The different kind elements may be incorporated into particles by intermixing salts of different kind elements and adjusting the pH upon the production of the magnetic material. Alternatively, after the magnetic material particles are produced, the pH is adjusted or the salts of the respective different kind elements are added to adjust the pH, thereby precipitating on the surfaces of the particles.

An amount used of the magnetic material is 10 to 200 parts by mass, preferably 20 to 150 parts by mass based on 100 parts by mass of the binder resin. A number average particle size thereof is preferably 0.1 to 2 μm, more preferably 0.1 to 0.5 μm.

The magnetic material has magnetic properties of 20 to 150 oersteds of coercive force, 50 to 200 emu/g of saturated magnetization, and 2 to 20 emu/g of remanent magnetization when 10K oersteds is applied. The magnetic material may also be used as the coloring agent.

(4) Other Additives

To the toner according to the present embodiment, other additives may be added as necessary for the purpose of protecting a photoreceptor or a carrier, improving cleaning properties, adjusting thermal properties, electrical properties and physical properties, adjusting resistance, adjusting a softening point, improving fixing properties and the like. Examples of other additives include a variety of metal soaps, a fluorochemical surfactant, dioctyl phthalate, a conductive agent such as tin oxide, zinc oxide, carbon black and antimony oxide, and inorganic fine powder such as titanium oxide, aluminum oxide and alumina. The inorganic fine powder may be hydrophobized as necessary. In addition, a lubricant such as polytetrafluoroethylene, zinc stearate and vinylidene polyfluoride, an abrasive such as cesium oxide, silicon carbide and strontium titanate, acaking prevention agent and a developing improver including white fine particles and black fine particles that have opposite polarity of the toner particles may be used in a minor amount.

The above-described respective additives may be treated with a treatment agent such as a silicone varnish, a variety of modified silicone varnishes, silicone oil, a variety of modified silicone oils, a silane coupling agent and an organic silicon compound.

[Carrier]

The toner according to the present embodiment may be mixed with a carrier and may be used as a two-component developer. The carrier has a role to add a chargeability to the toner by agitating with the toner and to add sufficient developability to the toner by carrying the toner to a developing area. As the carrier, a typical carrier such as ferrite and magnetite, and a resin coated carrier may be used.

The resin coated carrier includes carrier core particles and a covering material that is resin to cover (coat) the surfaces of the carrier core particles. Examples of the resin used in the covering material include styrene-acrylate resin, acrylate based resin, fluorine-containing resin, silicone resin, polyester resin, polyamide resin, polyvinyl butyral and amino acrylate resin. In addition, ionomer resin, polyphenylene sulfide resin may be used as the covering material of the carrier. Among them, a styrene-methyl methacrylate copolymer, a mixture of fluorine-containing resin, a styrene based copolymer or silicone resin are preferable. Silicone resin is more preferable. The resin may be used alone or in combination of plural ones.

Furthermore, a binder type carrier core including magnetic powder dispersed in resin may be used. The surface of the carrier core is at least covered with the resin covering material by a method of dissolving or suspending resin in a solvent and applying it to the carrier core, or a method of simply mixing in a powder state. A percentage of the resin covering material to the resin coated carrier may be determined as appropriate, but is preferably 0.01 to 5% by mass, more preferably 0.1 to 1% by mass to the resin coated carrier.

As the magnetic material of the carrier core, an oxide such as ferrite, iron excessive type ferrite, magnetite and $\gamma$-oxide, a metal such as iron, cobalt and nickel, and an alloy thereof. Examples of the elements included in the magnetic material include iron, cobalt, nickel, aluminum, copper, lead, magnesium, tin, zinc, antimony, beryllium, bismuth, calcium, manganese, selenium, titanium, tungsten and vanadium. Preferable examples include copper-zinc-iron based ferrite mainly including copper, zinc and iron and manganese-magnesium-iron based ferrite mainly including manganese, magnesium and iron.

A resistance value of the carrier may be $10^6$ to $10^{10}$ $\Omega \cdot cm$ by adjusting an irregularity degree of the carrier surface and the amount of the covering resin. The particle size of the carrier may be 4 to 20 µm, preferably 10 to 150 µm, more preferably 20 to 100 µm. In particular, the resin coat carrier preferably has 50% particle size of 20 to 70 µm.

In the two-component developer, preferably 1 to 200 parts by mass, more preferably 2 to 50 parts by mass of the toner according to the present embodiment is preferably used based on 100 parts by mass of the carrier.

[Production Method of Toner]

The toner according to the present embodiment may be produced by a known method. The production method is roughly classified into a pulverization method and a polymerization method. In the present specification, the toner provided by the pulverization method is called as pulverized toner, and the toner provided by the polymerization method is called as polymerized toner.

The pulverization method is to sufficiently mix the above-described constituent materials such as the binder resin, the charge control agent and the coloring agent using a mixer such as a ball mill, to knead the mixture using a heating kneader such as a thermal roll kneader, cool, solidify, pulverize and classify the mixture. Alternatively, the mixture may be dissolved in a solvent, atomized by a spray, dried and classified.

In an external addition method, the charge control agent, the additives and the toner are sufficiently mixed and agitated using a mixer such as a Henschel mixer, a ball mill, a Nauta mixer, a V type mixer, a W type mixer and a super mixer to externally add them uniformly to the surfaces of the toner particles, thereby providing intended toner for electrostatic development.

The polymerization method is to mix, emulsify or suspend, and polymerize a monomer constituting binder resin with predetermined materials, thereby providing the toner. In so-called microcapsule toner including a core material and a shell material, the toner may be produced by adding the predetermined materials to the core material, the shell material or both. Alternatively, the toner may be produced by sufficiently mixing the predetermined additives and the toner particles using a mixer such as a Henschel mixer as necessary.

Examples of the polymerization method include a suspension polymerization method, an emulsion coagulation method and an emulsion polymerization method. In the suspension polymerization method, the polymerizable monomer, the coloring agent, the polymerization initiator, the charge control agent are uniformly dissolve or disperse together with the cross-linking agent, a dispersion stabilizer and other additives as necessary to prepare a monomer composition. The monomer composition and the dispersion stabilizer are dispersed into a continuous phase, e.g., a water phase. Granulation may be done by adjusting an agitation speed, a temperature and a time so that droplets of the polymerizable monomer composition have desirable sizes for the toner particles. At the same time, a polymerization reaction is done at 40 to 90° C., thereby providing the toner particles having desirable particle size. The resultant toner particles are cleaned, filtered out and dried. The external addition treatment after the production of the toner particles may be executed by the method mentioned above.

In the emulsion coagulation method, a variety of dispersion liquid including the toner particles such as the charge control agent dispersion and the binder resin dispersion is prepared. At this time, the charge control agent dispersion, the binder resin dispersion and other toner components may be mixed and prepared as necessary. Through a step of coagulating the mixture liquid to form coagulated particles, a step of heating the coagulated particles to be fused, a step of washing and a step of drying, the toner particles may be provided. The respective dispersion liquid may be produced by using a dispersion such as a surfactant.

The emulsion polymerization method is to emulsify and disperse the polymerizable monomer for providing the binder resin and resin particles supporting the coloring agent in an aqueous medium, to which a water-soluble polymerization initiator is added, heated and polymerized. The toner particles obtained by the emulsion polymerization method have excellent uniformity as compared with the particles obtained by the suspension polymerization method, but has a volume average particle size as extremely small as 0.1 to 1.0 μm. In some cases, the toner may be produced by so-called seed polymerization where emulsified particles are used as a core and a polymerizable monomer is added thereafter to grow the particles, or by a method for unifying and fusing emulsified particles to a suitable average particle size.

By these polymerization methods, the toner particles are produced without pulverization. Therefore, applying brittleness to the toner particles is unnecessary, and a large amount of the materials having a low softening point that are difficult to be used in the pulverization method in the related art may be used. Thus, it enlarges the range of material choice. In addition, a releasing agent or a coloring agent that is a hydrophobic material is difficult to be exposed. Therefore, a toner supporting member, a photoreceptor, a transfer roller and a fixing unit may be less contaminated.

By these polymerization methods, the toner having a small average particle size and a sharp particle size distribution may be relatively easily provided, which is capable of forming microdots. That is to say, the toner provided by the polymerization methods has improved properties including image reproducibility, transfer properties and color reproducibility.

The pulverized toner according to the present embodiment has a volume average particle size of preferably 2 to 15 μm, more preferably 3 to 12 μm. When the volume average particle size is 15 μm or less, resolution and sharpness may be improved. When the volume average particle size is 2 μm or more, a high-cost problem due to yield deterioration upon the toner production, and health impairment such as toner scattering in-machine and skin permeation may be prevented.

On the other hand, the polymerized toner has a volume average particle size of preferably 3 to 9 μm, more preferably 4 to 8.5 μm, most preferably 5 to 8 μm. When the volume average particle size is 4 μm or more, toner flowability is improved and a charging property of each particle may be improved. Also, a charge distribution is narrowed, thereby inhibiting background fog and toner leak from a developing unit. In addition, cleaning is easily done. When the volume average particle size is 9 μm or less, resolution is improved and a high image quality is provided.

As the toner according to the present embodiment includes the charge control agent A, a charge rise speed is high, a charge amount is high, and a charging property, especially an environmental stability, is excellent. Also, as the toner has no heavy metals that have a problem concerning the waste regulation, a burden applied to human and environment may be decreased, and dispersibility and a compound stability are excellent.

The toner according to the present embodiment may be used in a one component development system and a two component development system. The one component development system is to feed a thin toner film to a latent image support and to develop a latent image. The thin toner film is produced using a device having a toner transport member, a toner layer thickness regulating member and a toner supply auxiliary member, and the supply auxiliary member is in contact with the toner transport member, and the toner layer thickness regulating member is in contact with the toner transport member.

The two component development system uses a toner and a carrier. As the carrier, the above-described magnetic material and glass beads are used. The developing agent (toner and carrier) are agitated by an agitating member to generate a predetermined charge amount, and is transported to a developing site by a magnetic roller, etc. On the magnet roller, the developing agent is held on a surface of the roller by a magnetic force, and a magnetic brush is formed to have a layer regulated to a suitable height by a developing agent regulating plate. The developing agent moves on the roller accompanied by a rotation of a developing roller, and is made facing to an electrostatic latent image holder in a contact state or a non-contact state at regular intervals, thereby developing and visualizing the latent image. In the case of developing in a non-contact state, a direct electric field is generally generated between the developing agent and the latent image holder, thereby providing a driving force to fly the toner in a space at the regular intervals. In order to develop a more clear image, the toner may be applicable to a system for superimposing alternating current.

EXAMPLES

Hereinbelow, the present invention will be described in detail by referring to Examples and Comparative Examples, but is not limited thereto. Note that in Examples, all "parts" represent "parts by mass".

<Synthesis of Bisphthalimide Derivative>

The bisphthalimide derivative represented by the formula (1) was purified by a column chromatography, adsorption with silica gel, activated carbon or activated clay, recrystallization with solvent or crystallization method. The compound is identified by an NMR analysis.

Example 1

Synthesis of Compound 3

To a nitrogen-purged reaction vessel, 180 ml of xylene, 10.0 g (31 mmol) of benzophenone tetracarboxylic dianhydride, 6.3 g (68.2 mmol) of aniline and 18 ml of dimethylacetamide were added, which was heated and refluxed for 8 hours while by-product water was evacuated. After cooling, a resultant product was filtered and collected, dispersed and washed with cyclohexane, then dried at 60° C. under reduced pressure, thereby providing 12.5 g of pale yellow crystal (yield 85%).

A structure of resultant pale yellow crystal was identified using NMR. At $^1$H-NMR (DMSO-$d_6$), the following 16 hydrogen signals were detected. δ (ppm)=7.29 (4H), 7.38 (6H), 8.28 (4H), 8.42 (2H).

Example 2

Synthesis of Compound 5

To a nitrogen-purged reaction vessel, 180 ml of xylene, 10.0 g (31 mmol) of benzophenone tetracarboxylic dianhydride, 7.3 g (68.2 mmol) of o-toluidine and 18 ml of dimethylacetamide were added, which was heated and refluxed for 8 hours while by-product water was evacuated. After cooling, a resultant product was filtered and collected, dispersed and washed with cyclohexane, then dried at 60° C. under reduced pressure, thereby providing 12.1 g of pale yellow crystal (yield 78%).

A structure of resultant pale yellow crystal was identified using NMR. At $^1$H-NMR (DMSO-$d_6$), the following 20 hydrogen signals were detected. δ (ppm)=2.14 (6H), 7.27 (2H), 7.43 (2H), 7.66 (4H), 8.26 (4H), 8.40 (2H).

Example 3

Synthesis of Compound 9

To a nitrogen-purged reaction vessel, 180 ml of xylene, 10.0 g (31 mmol) of benzophenone tetracarboxylic dianhydride, 8.7 g (68.2 mmol) of m-chloroaniline and 18 ml of dimethylacetamide were added, which was heated and refluxed for 8 hours while by-product water was evacuated. After cooling, a resultant product was filtered and collected, dispersed and washed with cyclohexane, then dried at 60° C. under reduced pressure, thereby providing 14.8 g of pale yellow crystal (yield 88%).

A structure of resultant pale yellow crystal was identified using NMR. At $^1$H-NMR (DMSO-$d_6$), the following 14 hydrogen signals were detected. δ (ppm)=7.18 (2H), 7.34 (4H), 7.71 (2H), 8.28 (4H), 8.42 (2H).

Example 4

Synthesis of Compound 11

To a nitrogen-purged reaction vessel, 180 ml of xylene, 10.0 g (31 mmol) of benzophenone tetracarboxylic dianhydride, 8.4 g (68.2 mmol) of o-anisidine and 18 ml of dimethylacetamide were added, which was heated and refluxed for 8 hours while by-product water was evacuated. After cooling, a resultant product was filtered and collected, dispersed and washed with cyclohexane, then dried at 60° C. under reduced pressure, thereby providing 13.9 g of pale yellow crystal (yield 84.2%).

A structure of resultant pale yellow crystal was identified using NMR. At $^1$H-NMR (DMSO-$d_6$), the following 20 hydrogen signals were detected. δ (ppm)=3.76 (6H), 7.11 (2H), 7.24 (2H), 7.41 (2H), 7.51 (2H), 8.21 (6H).

Example 5

Synthesis of Compound 16

To a nitrogen-purged reaction vessel, 200 ml of xylene, 12.0 g (37.2 mmol) of benzophenone tetracarboxylic dianhydride, 9.0 g (82 mmol) of p-aminophenol and 20 ml of dimethylacetamide were added, which was heated and refluxed for 4 hours while by-product water was evacuated. After cooling, a resultant product was filtered and collected, dispersed and washed with acetone, then dried at 60° C. under reduced pressure, thereby providing 15.8 g of pale yellow crystal (yield 84%).

A structure of resultant pale yellow crystal was identified using NMR. At $^1$H-NMR (DMSO-$d_6$), the following 16 hydrogen signals were detected. δ (ppm)=6.88 (4H), 7.23 (4H), 8.12 (4H), 8.24 (2H), 9.62 (2H).

Example 6

Synthesis of Compound 17

To a nitrogen-purged reaction vessel, 200 ml of xylene, 12.0 g (37.2 mmol) of benzophenone tetracarboxylic dianhydride, 8.8 g (82 mmol) of benzylamine and 20 ml of dimethylacetamide were added, which was heated and refluxed for 4 hours while by-product water was evacuated. After cooling, a resultant product was filtered and collected, dispersed and washed with cyclohexane, then dried at 60° C. under reduced pressure, thereby providing 9.1 g of pale yellow crystal (yield 49%).

A structure of resultant pale yellow crystal was identified using NMR. At $^1$H-NMR (CDCl$_3$), the following 20 hydrogen signals were detected. δ (ppm)=4.89 (4H), 7.28 (6H), 7.44 (4H), 7.99 (2H), 8.14 (4H).

Example 7

Synthesis of Compound 19

To a nitrogen-purged reaction vessel, 180 ml of xylene, 10.0 g (31 mmol) of benzophenone tetracarboxylic dianhydride, 8.8 g (68.2 mmol) of n-octylamine and 18 ml of dimethylacetamide were added, which was heated and refluxed for 4 hours while by-product water was evacuated. After solvent distillation, a resultant product was dispersed and washed with methanol and cyclohexane in order, then dried at 60° C. under reduced pressure, thereby providing 11.1 g of pale yellow crystal (yield 65.2%).

A structure of resultant pale yellow crystal was identified using NMR. At $^1$H-NMR (CDCl$_3$), the following 34 hydrogen signals were detected. δ (ppm)=0.87 (6H), 1.29 (20H), 3.73 (2H), 8.00 (2H), 8.18 (4H).

Example 8

Synthesis of Compound 20

To a nitrogen-purged reaction vessel, 200 ml of xylene, 15.0 g (46.5 mmol) of benzophenone tetracarboxylic dianhydride, 6.6 g (102.3 mmol) of 2-aminoethanol and 20 ml of dimethylacetamide were added, which was heated and refluxed for 4 hours while by-product water was evacuated. After cooling, a resultant product was dissolved into DMF, collected by filtering precipitated crystal with addition of water, then dried at 60° C. under reduced pressure, thereby providing 6.0 g of brown crystal (yield 32.0%).

A structure of resultant brown crystal was identified using NMR. At $^1$H-NMR (DMSO-$d_6$), the following 16 hydrogen signals were detected. δ (ppm)=3.64 (8H), 4.88 (2H), 8.06 (4H), 8.19 (2H).

Example 9

Synthesis of Compound 22

To a nitrogen-purged reaction vessel, 180 ml of xylene, 10.0 g (31.0 mmol) of benzophenone tetracarboxylic dianhydride, 6.8 g (68.2 mmol) of cyclohexylamine and 18 ml of dimethylacetamide were added, which was heated and refluxed for 4 hours while by-product water was evacuated. After cooling, a resultant product was filtered and collected, dispersed and washed with cyclohexane, then dried at 60° C. under reduced pressure, thereby providing 10.5 g of white crystal (yield 70%).

A structure of resultant white crystal was identified using NMR. At $^1$H-NMR (CDCl$_3$), the following 28 hydrogen signals were detected. δ (ppm)=1.36 (6H), 1.75 (10H), 2.21 (4H), 4.16 (2H), 7.98 (2H), 8.14 (4H).

Example 10

Synthesis of Compound 23

To a nitrogen-purged reaction vessel, 180 ml of xylene, 10.0 g (31.0 mmol) of benzophenone tetracarboxylic dianhydride, 8.9 g (68.2 mmol) of 2-aminoethylmorpholine and 18 ml of dimethylacetamide were added, which was heated and refluxed for 4 hours while by-product water was evacuated. After cooling, a resultant product was filtered and collected, dissolved into chloroform, and crystallized by adding methanol. The precipitated crystal was filtered and collected, then dried at 60° C. under reduced pressure, thereby providing 7 g of pale brown crystal (yield 41%).

A structure of resultant pale brown crystal was identified using NMR. At $^1$H-NMR (CDCl$_3$), the following 30 hydrogen signals were detected. δ (ppm)=2.53 (8H), 2.66 (4H), 3.64 (8H), 3.87 (4H), 8.02 (2H), 8.18 (4H).

Example 11

Synthesis of Compound 24

To a nitrogen-purged reaction vessel, 200 ml of xylene, 12.0 g (37.2 mmol) of benzophenone tetracarboxylic dianhydride, 7.7 g (82 mmol) of 2-pyridylamine and 20 ml of dimethylacetamide were added, which was heated and refluxed for 4 hours while by-product water was evacuated. After cooling, a resultant product was filtered and collected, dispersed and washed with cyclohexane, then dried at 60° C. under reduced pressure, thereby providing 12.3 g of white crystal (yield 69.5%).

A structure of resultant white crystal was identified using NMR. At $^1$H-NMR (DMSO-d$_6$), the following 14 hydrogen signals were detected. δ (ppm)=7.00 (2H), 7.40 (2H), 7.73 (2H), 8.29 (4H), 8.44 (2H), 8.51 (2H).

Example 12

Synthesis of Compound 47

To a nitrogen-purged reaction vessel, 1000 ml of xylene, 50.0 g (170 mmol) of biphenyl tetracarboxylic dianhydride, 27.3 g (370 mmol) of n-buthylamine and 100 ml of dimethylacetamide were added, which was heated and refluxed for 5 hours while by-product water was evacuated. After cooling, a resultant product was filtered and collected, dispersed and washed with methanol, then dried at 60° C. under reduced pressure, thereby providing 62.2 g of pale yellow crystal (yield 68.3%).

A structure of resultant pale yellow crystal was identified using NMR. At $^1$H-NMR (CDCl$_3$), the following 24 hydrogen signals were detected. δ (ppm)=0.96 (6H), 1.39 (4H), 1.69 (4H), 3.73 (4H), 7.97 (4H), 8.10 (2H).

Example 13

Synthesis of Compound 48

To a nitrogen-purged reaction vessel, 200 ml of xylene, 8.0 g (27.2 mmol) of biphenyl tetracarboxylic dianhydride, 7.6 g (59.8 mmol) of cyclooctylamine and 20 ml of dimethylacetamide were added, which was heated and refluxed for 6 hours while by-product water was evacuated. After cooling, a resultant product was filtered and collected, dispersed and washed with acetone, then dried at 60° C. under reduced pressure, thereby providing 12.8 g of white crystal (yield 92.1%).

A structure of resultant white crystal was identified using NMR. At $^1$H-NMR (CDCl$_3$), the following 36 hydrogen signals were detected. δ (ppm)=1.58-1.86 (24H), 2.31-2.37 (4H), 4.40 (2H), 7.94 (4H), 8.05 (2H).

Example 14

Synthesis of Compound 49

To a nitrogen-purged reaction vessel, 200 ml of xylene, 8.0 g (27.2 mmol) of biphenyl tetracarboxylic dianhydride, 6.4 g (59.8 mmol) of benzylamine and 20 ml of dimethylacetamide were added, which was heated and refluxed for 4 hours while by-product water was evacuated. After cooling, a resultant product was filtered and collected, dispersed and washed with methanol, then dried at 60° C. under reduced pressure, thereby providing 10.1 g of pale yellow crystal (yield 78.9%).

A structure of resultant pale yellow crystal was identified using NMR. At $^1$H-NMR (CDCl$_3$), the following 20 hydrogen signals were detected. δ (ppm)=4.88 (4H), 7.27 (2H), 7.33 (4H), 7.45 (4H), 7.94-7.96 (4H), 8.08 (2H).

Example 15

Synthesis of Compound 50

To a nitrogen-purged reaction vessel, 200 ml of xylene, 10.0 g (31 mmol) of benzophenone tetracarboxylic dianhydride, 9.7 g (68.2 mmol) of 4-chloro-2-methylaniline and 20 ml of dimethylacetamide were added, which was heated and refluxed for 6 hours while by-product water was evacuated. After cooling, a resultant product was filtered and collected, dispersed and washed with methanol, then dried at 60° C. under reduced pressure, thereby providing 15.0 g of pale yellow crystal (yield 85%).

A structure of resultant pale yellow crystal was identified using NMR. At $^1$H-NMR (DMSO-d$_6$), the following 18 hydrogen signals were detected. δ (ppm)=3.14 (6H), 7.27 (2H), 7.43 (2H), 7.66 (4H), 8.26 (2H), 8.53 (2H).

Example 16

Synthesis of Compound 51

To a nitrogen-purged reaction vessel, 200 ml of xylene, 10.0 g (31 mmol) of benzophenone tetracarboxylic dianhydride, 6.0 g (82.0 mmol) of 2-amino-4-chlorophenol and 20 ml of dimethylacetamide were added, which was heated and refluxed for 6 hours while by-product water was evacuated. After cooling, a resultant product was filtered and collected, dispersed and washed with methanol, then dried at 60° C. under reduced pressure, thereby providing 11.1 g of pale yellow crystal (yield 62.1%).

A structure of resultant pale yellow crystal was identified using NMR. At $^1$H-NMR (DMSO-d$_6$), the following 14 hydrogen signals were detected. δ (ppm)=6.97 (2H), 7.34 (2H), 7.41 (2H), 8.14 (4H), 8.22 (2H), 10.22 (2H).

Example 17

Synthesis of Compound 52

To a nitrogen-purged reaction vessel, 200 ml of xylene, 10.0 g (27.9 mmol) of diphenyl sulfone tetracarboxylic dianhydride, 7.6 g (61.4 mmol) of 4-amino-m-cresol and 20 ml of dimethylacetamide were added, which was heated and refluxed for 6.5 hours while by-product water was evacuated. After cooling, a resultant product was filtered and collected, dispersed and washed with methanol, then dried at 60° C. under reduced pressure, thereby providing 13.1 g of pale yellow crystal (yield 82.4%).

A structure of resultant pale yellow crystal was identified using NMR. At $^1$H-NMR (DMSO-d$_6$), the following 20 hydrogen signals were detected. δ (ppm)=2.01 (6H), 6.70 (2H), 6.76 (2H), 7.11 (2H), 8.20 (2H), 8.21 (6H).

Example 18

<Production of Non-Magnetic Toner 1>

91 parts of styrene-acrylate based copolymer resin (manufactured by Mitsui Chemicals, Inc. under a product name of CPR-100, acid value of 0.1 mgKOH/g), 1 part of the bisphthalimide derivative (compound 5) synthesized in Example 2, 5 parts of carbon black (manufactured by Mitsubishi Chemicals, Inc. under a product name of MA-100) and 3 parts of low molecular weight polypropylene (manufactured by Sanyo Chemical Industries, Inc. under a product name of Biscol 550P) were melted and mixed in a heating mixer (biaxial extrusion kneader) at 130° C. The mixture cooled was roughly pulverized using a Hammer mill, finely pulverized using a jet mill, and classified to provide non-magnetic toner 1 having a volume average particle size of 9±0.5 μm.

<Evaluation of Non-Magnetic Toner 1>

Four parts of the resultant non-magnetic toner 1 was mixed and shaken with 100 parts of a non-coat type ferrite carrier (F-150 manufactured by Powdertech Co., Ltd.) to negatively charge the toner. Thereafter, a charge amount was measured under atmosphere of a temperature of 25° C. and a humidity of 50% using a blow-off charge amount measuring device.

In addition, the resultant non-magnetic toner 1 was mixed with a silicon coat type ferrite carrier (F96-150 manufactured by Powdertech Co., Ltd.) to evaluate a charge amount.

Example 19

<Production and Evaluation of Non-Magnetic Toner 2>

Non-magnetic toner 2 having a volume average particle size of 9±0.5 μm was prepared under the similar conditions in Example 18 except that the bisphthalimide derivative (compound 9) synthesized in Example 3 was used in place of the compound 5 used as the charge control agent in Example 18, and a charge amount thereof was evaluated using the blow-off charge amount measuring device.

Example 20

<Production and Evaluation of Non-Magnetic Toner 3>

Non-magnetic toner 3 having a volume average particle size of 9±0.5 μm was prepared under the similar conditions in Example 18 except that the bisphthalimide derivative (compound 22) synthesized in Example 9 was used in place of the compound 5 used as the charge control agent in Example 18, and a charge amount thereof was evaluated using the blow-off charge amount measuring device.

Example 21

<Production and Evaluation of Non-Magnetic Toner 4>

Non-magnetic toner 4 having a volume average particle size of 9±0.5 μm was prepared under the similar conditions in Example 18 except that the bisphthalimide derivative (compound 47) synthesized in Example 12 was used in place of the compound 5 used as the charge control agent in Example 18, and a charge amount thereof was evaluated using the blow-off charge amount measuring device.

Example 22

<Production and Evaluation of Non-Magnetic Toner 5>

Non-magnetic toner 5 having a volume average particle size of 9±0.5 μm was prepared under the similar conditions in Example 18 except that the bisphthalimide derivative (compound 52) synthesized in Example 17 was used in place of the compound 5 used as the charge control agent in Example 18, and a charge amount thereof was evaluated using the blow-off charge amount measuring device.

Comparative Example 1

<Production and Evaluation of Comparative Non-Magnetic Toner>

For comparison, non-magnetic toner was prepared under the similar conditions in Example 18 except that a salt of 3,5-tert-butylsalicylic acid and zinc (comparative compound 1) was used in place of the bisphthalimide derivative (compound 5) synthesized in Example 2 used as the charge control agent in Example 18, and a charge amount thereof was evaluated using the blow-off charge amount measuring device.

[Evaluation Results of Non-Magnetic Toner]

Table 1 shows the charge control agent added and the charge amount [μC/g] measured in each non-magnetic toner in Examples 18 to 22 and Comparative Example 1.

TABLE 1

| | | Charge amount (μC/g) | |
|---|---|---|---|
| | Charge control agent | Carrier F-150 | Carrier F96-150 |
| Example 18 | Compound 5 | −55.0 | −32.6 |
| Example 19 | Compound 9 | −58.2 | −43.2 |
| Example 20 | Compound 22 | −57.8 | −39.5 |
| Example 21 | Compound 47 | −57.3 | −33.9 |
| Example 22 | Compound 52 | −58.5 | −34.4 |
| Comparative Example 1 | Comparative compound 1 | −31.1 | −15.6 |

As apparent from the results shown in Table 1, each non-magnetic toner using the charge control agent A including the bisphthalimide derivative represented by the formula (1) provided the charge amount higher than that in Comparative Example.

Example 23

<Production of Polymerized Toner 1>

Among the polymerization methods, polymerized toner 1 was produced using the emulsion coagulation method. Respective steps performed will be described below.

[Preparation of Resin Dispersion Liquid]

80 parts of polyester resin (DIACRON ER-561 manufactured by Mitsubishi rayon Co., Ltd.), 320 parts of ethyl acetate and 32 parts of isopropyl alcohol were mixed. While the mixture was agitated at 5000 to 10000 rpm using a homogenizer (a foam-less mixer, NGM-0.5 TB manufactured by Beryu corp.), 0.1% by mass of ammonia water was dropped in a proper amount to conduct phase-transfer emulsification. The emulsion was depressurized using an evaporator to remove solvent. In this manner, resin dispersion liquid was provided. Resin particles in the dispersion liquid had a volume average particle size of 0.2 μm (a resin particle concentration was adjusted to 20% by mass by deionized water).

[Preparation of Charge Control Agent Dispersion Liquid]

0.2 part of sodium dodecylbenzenesulfonate, 0.2 parts of Solbon T-20 (manufactured by TOHO CHEMICAL INDUSTRY Co., Ltd.) and 17.6 parts of deionized water were mixed and dissolved. To the mixture, 2.0 parts of the bisphthalimide derivative (compound 5) synthesized in Example 2 and zirconia beads (a particle size of the beads was 0.65 mmφ, equivalent to 15 ml) were added. The resultant mixture was dispersed in a paint conditioner (Red Devil No. 5400-5L manufactured by UNION N.J. (USA)) for three hours. Using a sieve, the zirconia beads were removed. By adjusting with deionized water, there was provided 10% by mass of charge control agent dispersion liquid.

[Preparation of Polymerized Toner]

To a reaction vessel equipped with a thermometer, a pH meter and an agitator, 125 parts of the resin dispersion liquid, 1.0 part of 20% by mass of sodium dodecylbenzenesulfonate and 125 parts of deionized water were added and agitated at 150 rpm for 30 minutes while the liquid temperature was controlled to 30° C. 1% by mass of a nitric acid solution was added thereto to adjust the pH to 3.0. The mixture was further agitated for 5 minutes. While the mixture was dispersed using a homogenizer (Ultra-turrax T-25 manufactured by IKA Japan), 0.125 parts of poly aluminum chloride was added and the liquid temperature was increased to 50° C. The mixture was further dispersed for 30 minutes. After 62.5 parts of the resin dispersion liquid and 4.0 parts of the charge control agent dispersion liquid were added, 1% by mass of the nitric acid solution was added to adjust the pH to 3.0, and the mixture was further dispersed for 30 minutes. While the mixture was agitated at 400 to 7000 rpm using the agitator, 8.0 parts of 5% by mass of a sodium hydroxide solution was added thereto, and the agitation was continued until the toner had the volume average particle size of 9.5 μm. After the liquid temperature was increased to 75° C., the mixture was further agitated for 2 hours. After it was confirmed that the volume average particle size became 6.0 μm and the particles were spheroidized, the particles were rapidly cooled using ice water. The resultant particles were filtered, collected, dispersed and washed with deionized water. Dispersing and washing were repeated until electroconductivity of a filtrate after dispersing was 20 μS/cm or less (measuring device: HORIBA ES-51 manufactured by HORIBA, Ltd.). Thereafter, the particles were dried by a dryer at 40° C., thereby providing toner particles. The resultant toner particles were sieved by a sieve having a 166 mesh sieve (90 μm aperture) to prepare polymerized toner 1.

<Evaluation of Polymerized Toner 1>

Two parts of the resultant polymerized toner 1 was mixed and shaken with 100 parts of a silicon coat type ferrite carrier (F96-150 manufactured by Powdertech Co., Ltd.) to negatively charge the toner. Thereafter, a charge amount was measured under atmosphere of a temperature of 25° C. and a humidity of 50% using a blow-off charge amount measuring device.

Example 24

<Production and Evaluation of Polymerized Toner 2>

Polymerized toner 2 was prepared under the similar conditions in Example 23 except that the bisphthalimide derivative (compound 47) synthesized in Example 12 was used in place of the compound 5 used as the charge control agent in Example 23, and a charge amount thereof was measured.

Example 25

<Production and Evaluation of Polymerized Toner 3>

Polymerized toner 3 was prepared under the similar conditions in Example 23 except that the bisphthalimide derivative (compound 52) synthesized in Example 17 was used in place of the compound 5 used as the charge control agent in Example 23, and a charge amount thereof was measured.

Comparative Example 2

<Production and Evaluation of Comparative Polymerized Toner>

Comparative polymerized toner was prepared under the similar conditions in Example 23 except that no charge control agent dispersion liquid was added as in Example 23, and a charge amount thereof was measured.

[Evaluation Results of Polymerized Toner]

Table 2 shows the charge control agent added and the charge amount [μC/g] measured in each polymerized toner in Examples 23 to 25 and Comparative Example 2.

TABLE 2

|  | Charge control agent | Charge amount (μC/g) Carrier F96-150 |
|---|---|---|
| Example 23 | Compound 5 | −60.2 |
| Example 24 | Compound 47 | −60.5 |
| Example 25 | Compound 52 | −61.2 |
| Comparative Example 2 | — | −21.5 |

As apparent from the results shown in Table 2, each polymerized toner using the charge control agent A including the bisphthalimide derivative represented by the formula (1) provided a high charge amount.

The above results reveals that the charge control agent A including the bisphthalimide derivative represented by the formula (1) has an excellent charging performance. By using the charge control agent A in the toner, the toner can be provided with an excellent charging performance.

Embodiments of the present invention are described above. The present invention is not to be limited to the above-described embodiments. It should be appreciated that various modifications and alterations may be made without departing from the scope and spirit of the present invention.

In this embodiment, the emulsion coagulation method is used for producing the polymerized toner as an example. It is not limited thereto, and other method for producing the polymerized toner may be used. For example, the suspension polymerization method and a dissolution suspension method may produce the polymerized toner having the similar charging property described above.

INDUSTRIAL APPLICABILITY

The bisphthalimide derivative represented by the formula (1) has an excellent charging performance. The charge control agent including the compound has a charging performance apparently higher than that of the charge control agent in the related art. The charge control agent is most suitable for color toner, especially for polymerized toner. Furthermore, extremely useful toner can be provided including no a heavy metal such as chromium that has a problem concerning the waste regulation.

The invention claimed is:

1. A charge control agent, comprising a bisphthalimide derivative represented by
a formula (1)

[Chemical Formula 1]

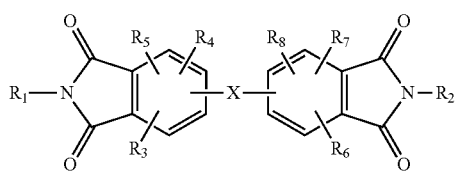

(1)

where when X represents a carbonyl group, $R_1$ and $R_2$ each represents a cycloalkyl group having 5 to 10 carbon atoms, an aromatic hydrocarbon group, a heterocyclic group or a fused polycyclic aromatic group, and when X represents a sulfur atom, a sulfinyl group, a sulfonyl group, or a single bond, $R_1$ and $R_2$ each represents a linear or branched alkyl group having 1 to 20 carbon atoms, a cycloalkyl group having 5 to 10 carbon atoms, an aromatic hydrocarbon group, a heterocyclic group, or a fused polycyclic aromatic group; $R_3$ to $R_8$ each represents a hydrogen atom, a deuterium atom, a halogen atom, a hydroxyl group, a cyano group, a trifluoromethyl group, a nitro group, a linear or branched alkyl group having 1 to 20 carbon atoms, a cycloalkyl group having 5 to 10 carbon atoms, a linear or branched alkenyl group having 2 to 6 carbon atoms, a linear or branched alkyloxy group having 1 to 8 carbon atoms, a cycloalkyloxy group having 5 to 10 carbon atoms, an aromatic hydrocarbon group, a heterocyclic group, a fused polycyclic aromatic group, or an aryloxy group.

2. A toner, comprising:
the charge control agent according to claim 1;
a coloring agent; and
a binder resin.

3. A polymerized toner, comprising:
the charge control agent according to claim 1;
a coloring agent; and
a binder resin.

4. A charge control agent, comprising a bisphthalimide derivative represented by
a formula (2)

[Chemical Formula 2]

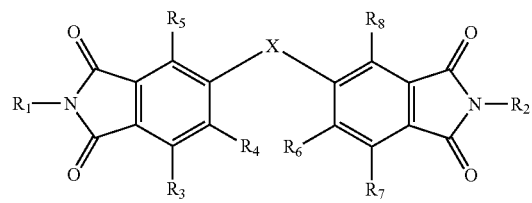

(2)

where when X represents a carbonyl group, $R_1$ and $R_2$ each represents a cycloalkyl group having 5 to 10 carbon atoms, an aromatic hydrocarbon group, a heterocyclic group or a fused polycyclic aromatic group, and when X represents a sulfur atom, a sulfinyl group, a sulfonyl group, or a single bond; $R_1$ and $R_2$ each represents a linear or branched alkyl group having 1 to 20 carbon atoms, a cycloalkyl group having 5 to 10 carbon atoms, an aromatic hydrocarbon group, a heterocyclic group, or a fused polycyclic aromatic group; $R_3$ to $R_8$ each represents a hydrogen atom, a deuterium atom, a halogen atom, a hydroxyl group, a cyano group, a trifluoromethyl group, a nitro group, a linear or branched alkyl group having 1 to 20 carbon atoms, a cycloalkyl group having 5 to 10 carbon atoms, a linear or branched alkenyl group having 2 to 6 carbon atoms, a linear or branched alkyloxy group having 1 to 8 carbon atoms, a cycloalkyloxy group having 5 to 10 carbon atoms, an aromatic hydrocarbon group, a heterocyclic group, a fused polycyclic aromatic group, or an aryloxy group.

5. A toner, comprising:
the charge control agent according to claim 4;
a coloring agent; and
a binder resin.

6. A polymerized toner, comprising:
the charge control agent according to claim 4;
a coloring agent; and
a binder resin.

7. A charge control agent, comprising a bisphthalimide derivative represented by a formula (2')

[Chemical Formula 2]

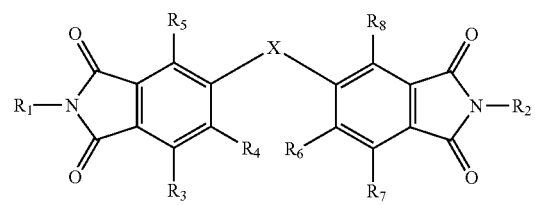

(2')

where when X represents a carbonyl group, $R_1$ and $R_2$ each represents a cycloalkyl group having 5 to 10 carbon atoms, an aromatic hydrocarbon group or a heterocyclic group, and when X represents a sulfonyl group, or a single bond; $R_1$ and $R_2$ each represents a linear or branched alkyl group having 1 to 20 carbon atoms, a cycloalkyl group having 5 to 10 carbon atoms, an aromatic hydrocarbon group, or a heterocyclic group; $R_3$ to $R_8$ each represents a hydrogen atom, a deuterium atom, a halogen atom, a hydroxyl group, a cyano group, a trifluoromethyl group, a nitro group, a linear or branched alkyl group having 1 to 20 carbon atoms, a cycloalkyl group having 5 to 10 carbon atoms, a linear or branched alkenyl group having 2 to 6 carbon atoms, a linear or branched alkyloxy group having 1 to 8 carbon atoms, or an aromatic hydrocarbon group.

8. A toner, comprising:
the charge control agent according to claim 7;
a coloring agent; and
a binder resin.

9. A polymerized toner, comprising:
the charge control agent according to claim 7;
a coloring agent; and
a binder resin.

* * * * *